United States Patent
Wyatt et al.

(10) Patent No.: US 10,053,659 B2
(45) Date of Patent: Aug. 21, 2018

(54) MODULAR TUBULAR BIOREACTOR

(71) Applicant: HELIAE DEVELOPMENT LLC, Gilbert, AZ (US)

(72) Inventors: Cameron Wyatt, Gilbert, AZ (US); Richard Mazur, Phoenix, AZ (US); James Riley, Gilbert, AZ (US); Thomas Kulaga, Chandler, AZ (US); Alexander Sitek, Gilbert, AZ (US); Jason Licamele, Scottsdale, AZ (US); Timothy Sullivan, Phoenix, AZ (US)

(73) Assignee: Heliae Development LLC, Gilbert, AZ (US)

( * ) Notice: Subject to any disclaimer, the term of this patent is extended or adjusted under 35 U.S.C. 154(b) by 232 days.

(21) Appl. No.: 14/812,713

(22) Filed: Jul. 29, 2015

(65) Prior Publication Data
US 2015/0329810 A1    Nov. 19, 2015

Related U.S. Application Data

(63) Continuation of application No. PCT/US2014/016490, filed on Feb. 14, 2014.

(60) Provisional application No. 61/769,605, filed on Feb. 26, 2013.

(51) Int. Cl.
| | |
|---|---|
| *C12M 1/00* | (2006.01) |
| *C12M 1/34* | (2006.01) |
| *C12M 1/12* | (2006.01) |
| *C12M 3/00* | (2006.01) |

(52) U.S. Cl.
CPC ............ *C12M 21/02* (2013.01); *C12M 23/00* (2013.01); *C12M 23/06* (2013.01); *C12M 23/44* (2013.01); *C12M 23/48* (2013.01); *C12M 27/20* (2013.01); *C12M 29/00* (2013.01); *C12M 31/02* (2013.01); *C12M 39/00* (2013.01); *C12M 41/12* (2013.01); *C12M 41/26* (2013.01); *C12M 41/32* (2013.01); *C12M 41/34* (2013.01)

(58) Field of Classification Search
CPC ................................ C12M 1/00; C12M 21/02
USPC ....................................................... 435/292.1
See application file for complete search history.

(56) References Cited

U.S. PATENT DOCUMENTS

| | | |
|---|---|---|
| 3,955,318 A | 5/1976 | Hulls |
| 8,101,080 B2 | 1/2012 | Robinson |

(Continued)

FOREIGN PATENT DOCUMENTS

| | | |
|---|---|---|
| DE | 102005025118 | 1/2007 |
| WO | 199409112 | 4/1994 |

(Continued)

OTHER PUBLICATIONS

IGV Biotech. Fotons for Future: Photobioreactor Product Catalog. Copyright 2012. Access online Feb. 20, 2013 at: http://www.igv-biotech.com/photobioreactor-scale-up.html.

*Primary Examiner* — Kevin Joyner
*Assistant Examiner* — Holly M Mull
(74) *Attorney, Agent, or Firm* — Heliae Development LLC; Veronica-Adele R. Cao

(57) ABSTRACT

Embodiments of a modular tubular bioreactor system for culturing an aqueous culture of microorganisms are described herein. The tubular bioreactor may comprise culture tubes configured in a vertically spaced and horizontally staggered arrangement to optimize the application of light to the culture in phototrophic and mixotrophic cultivation.

10 Claims, 30 Drawing Sheets

(56) References Cited

U.S. PATENT DOCUMENTS

| | | | |
|---|---|---|---|
| 2004/0259239 A1* | 12/2004 | Branson | C12M 21/02 435/292.1 |
| 2008/0311649 A1 | 12/2008 | Cloud | |
| 2010/0055765 A1 | 3/2010 | Frank | |
| 2010/0068779 A1 | 3/2010 | Wells | |
| 2010/0144023 A1* | 6/2010 | Weaver | C12M 21/02 435/292.1 |
| 2010/0151558 A1* | 6/2010 | Alianell | C12M 21/02 435/257.3 |
| 2011/0027875 A1 | 2/2011 | Cathcart | |
| 2011/0092726 A1 | 4/2011 | Clarke | |
| 2011/0201100 A1 | 8/2011 | Proulx | |
| 2011/0223076 A1 | 9/2011 | Wynn | |
| 2012/0021498 A1* | 1/2012 | Muller-Feuga | C12M 21/02 435/257.1 |
| 2012/0088296 A1 | 4/2012 | Vargas | |
| 2012/0107919 A1 | 5/2012 | Broneske | |
| 2012/0122199 A1 | 5/2012 | Kabakian | |
| 2012/0164712 A1 | 6/2012 | Ellem | |
| 2012/0202290 A1 | 8/2012 | Mueller-Rees | |
| 2012/0252105 A1 | 10/2012 | Ahrens | |
| 2013/0023043 A1 | 1/2013 | Hinkens | |
| 2013/0177966 A1 | 7/2013 | DePoli | |

FOREIGN PATENT DOCUMENTS

| | | |
|---|---|---|
| WO | 199506111 | 3/1995 |
| WO | 199946360 | 9/1999 |
| WO | 2007129327 | 11/2007 |
| WO | 2008010737 | 1/2008 |
| WO | 2009051478 | 4/2009 |
| WO | 2009051479 | 4/2009 |
| WO | 2009051480 | 4/2009 |
| WO | 2010014010 | 2/2010 |
| WO | 2010115412 | 10/2010 |
| WO | 2012019206 | 2/2012 |

\* cited by examiner

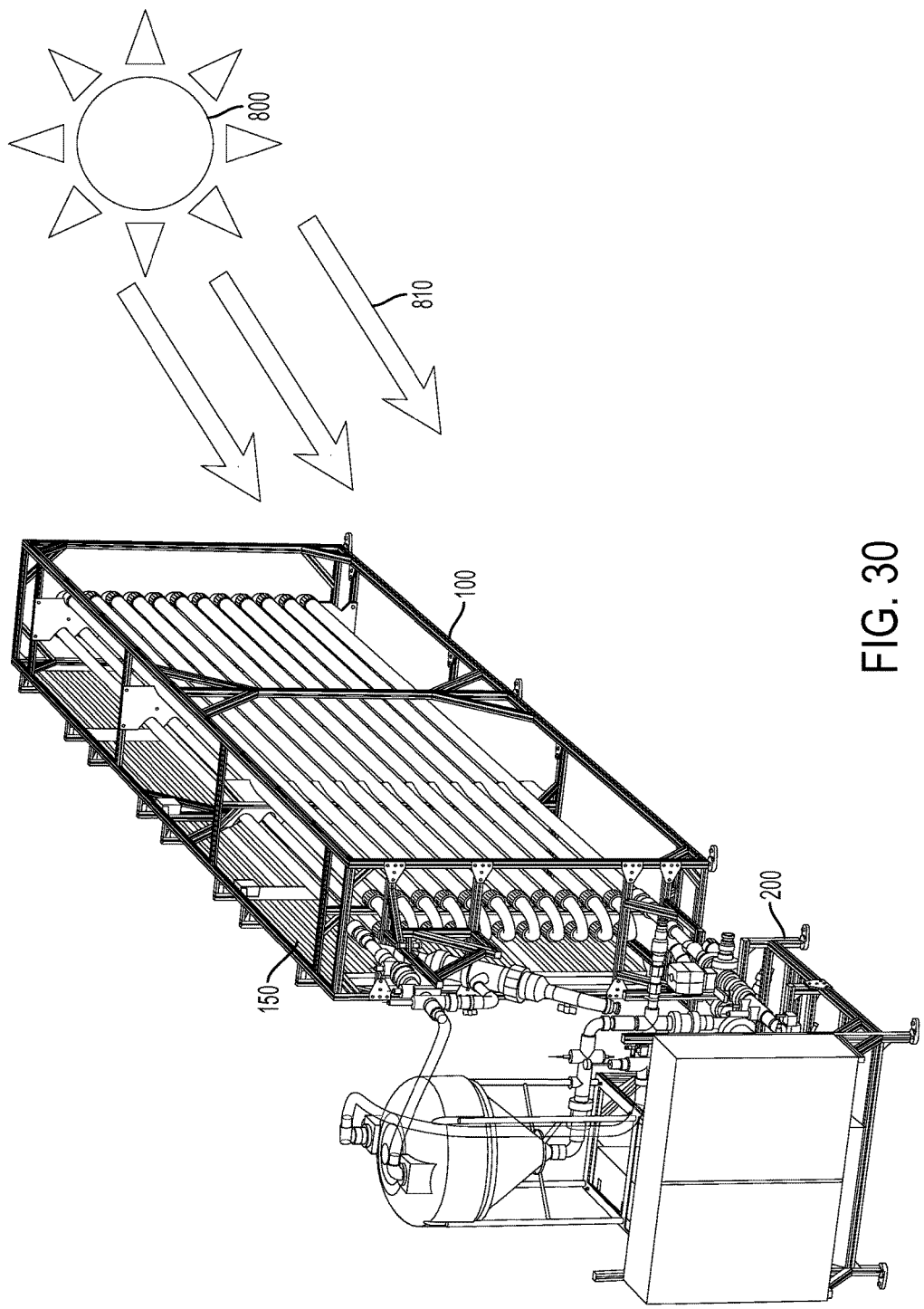

MODULAR TUBULAR BIOREACTOR

CROSS REFERENCE TO RELATED APPLICATIONS

This application claims the benefit of PCT Application No. PCT/US2014/016490, filed Feb. 14, 2014, entitled Modular Tubular Bioreactor, and U.S. Provisional Application No. 61/769,605, filed Feb. 26, 2013, entitled Modular Tubular Bioreactor, the entire contents of which are hereby incorporated by reference herein.

BACKGROUND

Microorganisms may be cultured in an aqueous medium to produce a variety of products such as lipids, proteins, pigments, and polysaccharides which may be used in the production of food, feed, fuel, pharmaceuticals, nutraceuticals, fertilizers, cosmetics, and plastics. Multiple bioreactor designs are capable of culturing microorganisms in an aqueous medium, including opened and closed bioreactor systems. A closed bioreactor system provides several advantages over an open bioreactor system, such as: the ability to shield the culture of microorganisms from outside contamination, the ability to limit water loss through evaporation, and the ability to better control the exchange of gasses between the microorganisms and the aqueous medium. The increased control provided by a closed bioreactor system also facilitates the ability to reproduce the quality of the harvested microorganisms, and meet requirements for containing genetically modified organisms. Closed bioreactor systems may comprise tubular, tank, bag, and panel bioreactors.

Tubular bioreactors may continuously circulate an aqueous culture in a single or plurality of flow paths provided by tubes in a straight, serpentine, helical, winding, or spiral arrangement. Tubular bioreactors have commonly been used for growth of microorganisms in phototrophic culture conditions, but tubular bioreactors may still experience drawbacks such as stagnation zones in the flow path, biofouling on the inner surface of the tubes and associated elbows or the de-gas tank, and inefficient engineering design which hampers reconfiguration or repair of the bioreactor system. Additionally, with the added complexity resulting in culture conditions comprising an organic carbon source, such as increased growth rate and production of gases in the culture, conventional tubular bioreactors used in phototrophic culture conditions are not well equipped to facilitate growth in mixotrophic or heterotrophic culture conditions, or switch between different culture conditions. Further, optimized designs for mixotrophic or heterotrophic systems may use tube diameters larger than those typically employed for phototrophic systems where short light path is needed to facilitate growth by availability of light. Optimized tube diameters for mixotrophic or heterotrophic systems may be larger than 10 cm and range from 10 to 100 cm. Tube diameters may range from 2 to 200 cm, with a preferred range for a phototrophic only system from 2 to 10 cm.

Tubular bioreactors known in the art are not designed optimally for commercial production. For example, engineering design of a conventional tubular bioreactor system is typically a single integrated system, which results in the entire tubular bioreactor system being unusable when a single component is not functional. Even when a non-functioning part may be isolated, the integrated system design is not optimal for upgrading or repairing the system. Also, the conventional single integrated tubular bioreactor system design is restricted to one configuration or set up, and does not have the flexibility to adapt to different configurations for different culture volumes or condition requirements. Also, material selection in a convention tubular bioreactor system, such as polyvinyl chloride (PVC) tubes, may result in unnecessary stagnation zones near connections, surface finish aggravated biofouling, or material degradation, causing suboptimal mixing or contamination of the microorganism culture.

In another example of sub-optimal design, a conventional tubular bioreactor system may space the tube segments for light application, but do not strategically configure the tube segments and lighting devices for optimal delivery of light to the aqueous culture of microorganisms within the tube and minimal light energy going unutilized by the microorganisms. Sub-optimal configuration of the tube segments may result in tube segments shading the aqueous culture disposed in other tube segments from light at certain locations, or a sub-optimal light path from the lighting source to the microorganisms. Additionally, sub-optimal positioning of lights can result in wasted light energy, which may be lighting more than the culture within the bioreactor tubes. Also, using conventional lighting systems may result in the application of harmful amounts of light or wavelengths of light which cannot be utilized by the microorganisms.

In an additional example of the limitations of conventional tubular bioreactors, a conventional tubular bioreactor engineered for phototrophic conditions may not be equipped to provide proper nutrients or gas exchange for mixotrophic and heterotrophic growth. The utilization of an organic carbon source in mixotrophic and heterotrophic cultures may increase the microorganism growth and culture density faster than a phototrophic bioreactor is equipped to handle. Also, the rate of gas saturation will differ from phototrophic cultures, as well as the oxygen and carbon dioxide production and consumption rates. A tubular bioreactor without the flexibility to accommodate various culture conditions limits the utility of the bioreactor for product production.

Therefore, there is a need in the art for a closed bioreactor system which is optimized for performance and provides the flexibility to accommodate different culture conditions.

SUMMARY

The application generally describes aspects of non-limiting embodiments for modular bioreactor systems for culturing an aqueous culture of microorganisms.

In one embodiment, a modular bioreactor system comprises: at least one bioreactor module comprising at least one coupling and configured to hold a circulating volume of an aqueous culture of microorganisms; at least one pump and control module comprising at least one coupling and configured to circulate a volume of the aqueous culture of microorganisms; and wherein each module is a standalone unit configured to be coupled to other bioreactor modules and pump and control modules for sealed fluid communication for the circulation of the aqueous culture, and configured to hold an isolated volume of the aqueous culture within each module when decoupled from other bioreactor modules and pump and control modules.

In some embodiments, the modular bioreactor system may further comprise at least one cleaning module comprising at least one coupling and configured to be coupled to at least one bioreactor module and at least one pump and control module. The at least one cleaning module may comprise a system utilizing at least one selected from the group consisting of PIG, swab and beads. In some embodiments, the bioreactor module may comprise a support frame and at least one culture tube. In some embodiments the pump and control module may comprise at least one pump and at least one selected from the group consisting of: a heat exchanger, a de-gas tank, a sensor, a gas supply device, a nutrient supply device, an organic carbon supply device, and a programmable logic control system.

In some embodiments, the gas supply device may be disposed before an intake of the pump in a flow path of the pump and control module. In some embodiments, wherein the sensors comprise at least one selected from the group consisting of, pH sensor, dissolved oxygen sensor, dissolved carbon dioxide sensor, temperature sensor. In some embodiments, the organic carbon supply device may supply an organic carbon source comprising at least one of selected from the group consisting of: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, saccharose, partial or complete hydrolysates of starch, sucrose, tartaric, TCA-cycle organic acids, thin stillage, urea, industrial waste solutions, and yeast extract.

In some embodiments, the at least one culture tube may comprise a plurality of tube segments connected in series. The plurality of tube segments connected in series may form a helical flow path. The at least one coupling is a quick connect coupling In another embodiment, a bioreactor module may comprise: a plurality of culture tube segments with a longitudinal axis along the length of the tube segments a circular cross section of a diameter D and an interior volume; and a support frame. The support frame may comprise at least one vertically oriented culture tube carrier configured to support the plurality of culture tube segments, on opposing horizontal sides of the carrier, in a horizontally staggered and vertically spaced arrangement wherein a horizontal plane intersecting the circular cross-section of at least one of the plurality of culture tube segments in a direction normal to the longitudinal axis of the culture tube segments and travels through the interior volume of at least one of the plurality of tube segments located on the horizontal plane a total distance less than or equal to D and greater than D/2.

In some embodiments, the plurality of culture tube segments are coupled together in series to form a single helical tubular flow path comprising: at least one U-bend culture tube segment; a plurality of straight culture tube segments; at least one connector configured to coupled together the ends of the at least one U-bend culture tube segment and the plurality of straight tube segments together in fluid communication in series to form a single helical tubular flow path. In some embodiments, the culture tube segments may comprise separate flow paths that are not connected. In some embodiments, at least one lighting device may be configured to emit light towards the plurality of culture tube segments. In some embodiments, 100% of the light emitted from the at least one lighting device traveling on a horizontal plane intersecting the circular cross-section of at least one of the plurality of culture tube segments in a direction normal to the longitudinal axis of the culture tube segments strikes the surface of the straight culture tube segments.

In another embodiment, a strategic lighting system for a tubular bioreactor system may comprise at least one lighting device disposed directly on an outer surface of at least one transparent tube segment, wherein the at least one lighting device is configured to emit light directly into the inner volume of the transparent tube segment through the transparent tube segment. The at least one lighting dive may comprise a plurality of lighting devices spaced along the at least one transparent tube segment. The at least one lighting device may be configured to apply continuous light to the inner volume of the transparent tube segment. In some embodiments, 99% of the light emitted by the at least one lighting device is transmitted into the inner volume of the transparent tube segment.

In some embodiments, the at least one lighting device may comprise a ring of light emitting diodes (LEDs). In some embodiments, the at least one lighting device may comprise a clamp with LEDs. In some embodiments, the plurality of lighting device may be spaced equally along the length of the at least one transparent tube segment. In some embodiments, the plurality of lighting device may be spaced at different lengths along the length of the at least one transparent tube segment. In some embodiments, the at least one transparent tube segment may be transparent at the location of the at least one lighting device and opaque at all other locations.

In another embodiment, a sensor manifold ma comprise: a seamless manifold comprising a curved wall profile and an interior volume; and at least one hollow bung comprising a base surface mirroring the profile of the manifold curved wall profile, welded directly to the manifold, and configured to hold and position at least one sensor within the interior volume of the manifold in a location which reduces the disruption to the fluid flow path through the manifold. In some embodiments, the manifold may comprise stainless steel. In some embodiments, the bung may further comprise an o-ring disposed at the base surface of the bung.

In another embodiment, a bioreactor system may comprise: bioreactor means configured for culturing an aqueous culture of microorganisms with access to at least some light; and pump and control means configured for circulating an aqueous culture of microorganisms, and supply at least one selected from the group consisting of a gas, a nutrient, and a carbon source. In some embodiments, the bioreactor system may further comprise cleaning means configured for cleaning surfaces of the bioreactor system.

BRIEF DESCRIPTION OF THE FIGURES

FIG. 30 shows a perspective view of an exemplary modular bioreactor system utilizing artificial and natural light.

DETAILED DESCRIPTION

Definitions

Figure 1:
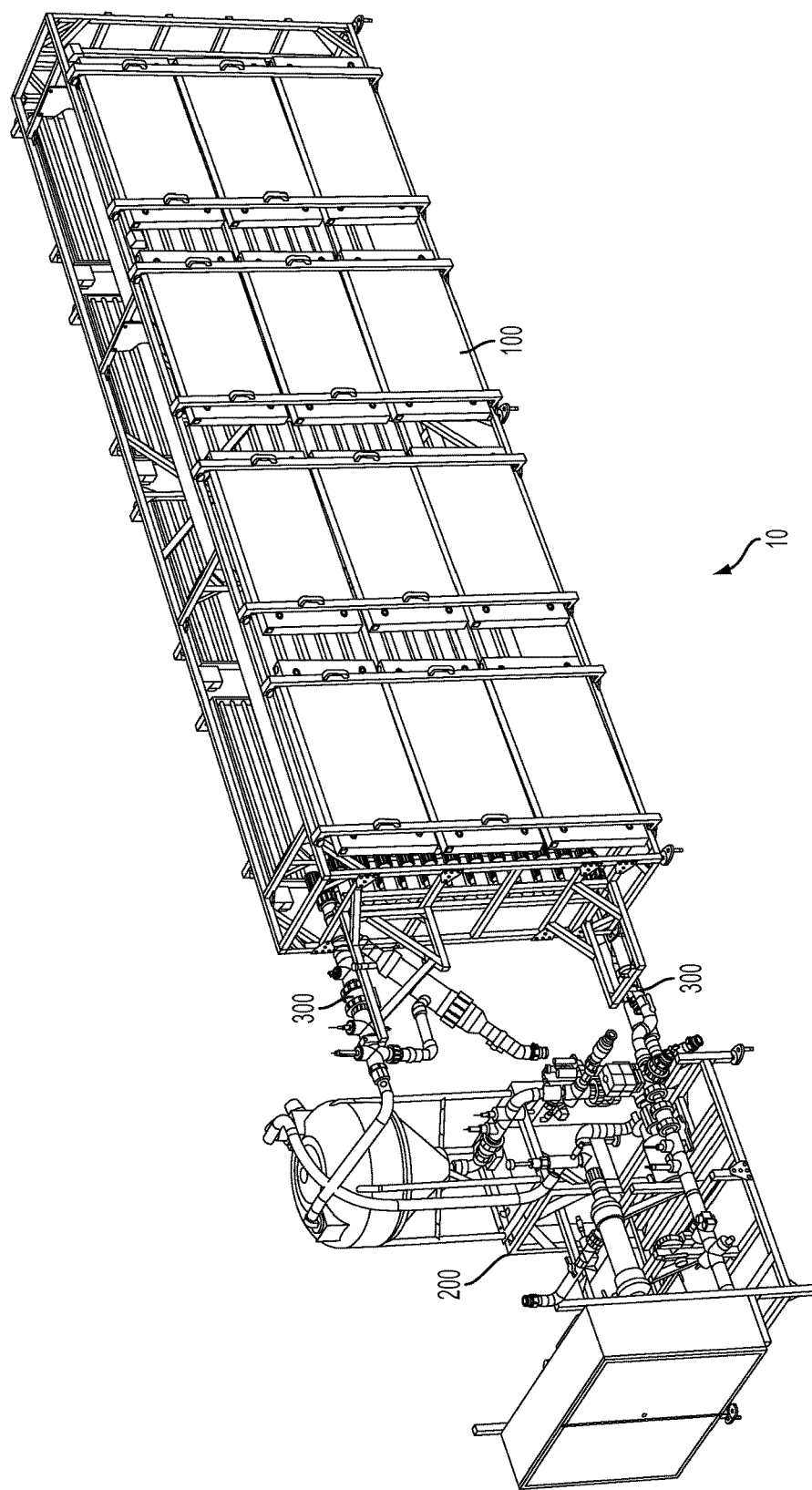
FIG. 1 shows a perspective view of an exemplary modular bioreactor system embodiment with the modules coupled together.

The term "microorganism" refers to microscopic organisms such as microalgae and cyanobacteria. Microalgae include microscopic multi-cellular plants (e.g. duckweed), photosynthetic microorganisms, heterotrophic microorganisms, diatoms, dinoflagelattes, and unicellular algae.

The terms "microbiological culture", "microbial culture", or "microorganism culture" refer to a method or system for multiplying microorganisms through reproduction in a pre-determined culture medium, including under controlled laboratory conditions. Microbiological cultures, microbial cultures, and microorganism cultures are used to multiply the organism, to determine the type of organism, or the abundance of the organism in the sample being tested. In liquid culture medium, the term microbiological, microbial, or microorganism culture generally refers to the entire liquid medium and the microorganisms in the liquid medium regardless of the vessel in which the culture resides. A liquid medium is often referred to as "media", "culture medium", or "culture media". The act of culturing is generally referred to as "culturing microorganisms" when emphasis is on plural microorganisms. The act of culturing is generally referred to as "culturing a microorganism" when importance is placed on a species or genus of microorganism. Microorganism culture is used synonymously with culture of microorganisms.

The terms "mixotrophic" and "mixotrophy" refer to culture conditions in which light, organic carbon, and inorganic carbon (e.g., carbon dioxide, carbonate, bi-carbonate) may be applied to a culture of microorganisms. Microorganisms capable of growing in mixotrophic conditions have the metabolic profile of both phototrophic and heterotrophic microorganisms, and may use both light and organic carbon as energy sources, as well as both inorganic carbon and organic carbon as carbon sources. A mixotrophic microorganism may be using light, inorganic carbon, and organic carbon through the phototrophic and heterotrophic metabolisms simultaneously or may switch between the utilization of each metabolism. A microorganism in mixotrophic culture conditions may be a net oxygen or carbon dioxide producer depending on the energy source and carbon source utilized by the microorganism. Microorganisms capable of mixotrophic growth comprise microorganisms with the natural metabolism and ability to grow in mixotrophic conditions, as well as microorganisms which obtain the metabolism and ability through modification of cells by way of methods such as mutagenesis or genetic engineering.

The terms "phototrophic", "phototrophy", "photoautotrophy", "photoautotrophic", and "autotroph" refer to culture conditions in which light and inorganic carbon (e.g., carbon dioxide, carbonate, bi-carbonate) may be applied to a culture of microorganisms. Microorganisms capable of growing in phototrophic conditions may use light as an energy source and inorganic carbon (e.g., carbon dioxide) as a carbon source. A microorganism in phototrophic conditions may produce oxygen.

The terms "heterotrophic" and "heterotrophy" refer to culture conditions in which organic carbon may be applied to a culture of microorganisms in the absence of light. Microorganisms capable of growing in heterotrophic conditions may use organic carbon as both an energy source and as a carbon source. A microorganism in heterotrophic conditions may produce carbon dioxide.

The term "light path" refers to the distance that light penetrates into a culture of microorganisms.

The term "duty cycle" refers to the fraction of the total light-dark microcycle in which an individual microorganism is exposed to light. Duty cycle is usually expressed as a percentage, wherein the percentage is the time of the microorganism exposed to light relative to the total time of the microorganism in the bioreactor system.

The term "frequency" when used in relation to the duty cycle refers to the number of times an individual microorganism completes the light-dark microcycle in a prescribed time period, and is usually expressed as Hertz (Hz) or cycles per second.

The term "lit section" refers to the portion of the bioreactor where the microorganism is exposed to light.

The term "quick connect", "quick connection", or "quick disconnect" refers to couplings of fluid transfer lines or conduits which may be operated by hand, are self-sealing, and do not include threaded connections or connections requiring tools (e.g., screwdriver, wrench) to secure and loosen the coupling.

The term "U-bend" refers to a 180 degree elbow joint.

Modular Bioreactor System

In one embodiment, a self-contained bioreactor system for culturing microorganisms in an aqueous medium comprises a modular bioreactor system. The modular bioreactor system comprises a plurality of modular components which may be easily coupled together into a functioning system and decoupled for repair, replacement, upgrading, shipping, cleaning, or reconfiguration. The interchangeability of the modular components allows components of a bioreactor system to be easily transported and assembled at multiple locations, as well as to change the capacity of the bioreactor system or change the functionality of the bioreactor system. Each module is a standalone unit that may be interchanged with other modular bioreactor systems for different configurations, providing the benefit of flexibility over conventional single configuration integrated bioreactor systems.

In some embodiments, the modular components may be decoupled when the modular bioreactor system contains an aqueous culture of microorganisms, while maintaining isolated volumes of the aqueous microorganism culture in the various individual modular components without exposing the culture of microorganisms to the environment or outside contamination. With the ability to maintain an isolated volume of the aqueous culture, modules may be interchanged in the event of equipment malfunction without necessitating harvest or enduring a complete loss of the microorganism culture. Additionally, an isolated volume of the aqueous microorganism culture may be transported to different locations for different operations, such as growth, product maturation (e.g., lipid accumulation, pigment accumulation), harvest, dewatering, etc. The modular components may couple and decouple from each other using pipe or tubular quick connect couplers which may be quickly coupled by hand to allow fluid communication between modular components and quickly decoupled in a manner which also self-seals any fluid communication, effectively sealing an isolated volume of the aqueous culture in each modular component. The quick connect couplers may comprise fluid conduit couplers known in the art such as, but not limited to, cam lock couplers.

In some embodiments, the modular bioreactor system may comprise at least one bioreactor module, and at least one pump and control module. In further embodiments, the modular bioreactor system may comprise at least one cleaning module. The modular bioreactor system may be capable of culturing microorganisms in phototrophic, mixotrophic, or heterotrophic conditions depending on the modular components selected, the configuration of the modular components selected, and the materials comprising the modular components. In some embodiments, the modular bioreactor system may functionally transition between phototrophic, mixotrophic, and heterotrophic culture conditions in any combination during the life of the aqueous culture of microorganisms. The transition between culture conditions may occur over a time range from seconds to days or may occur during a flow cycle through the bioreactor module. In some embodiments, the transition in culture conditions may comprise a functional change in the application of light, blocking of light, application of types or volume of gases, application of inorganic carbon (e.g., carbon dioxide), or application of organic carbon. In some embodiments, the modular bioreactor system may comprise equal numbers of each type of module. In some embodiments, the modular bioreactor system may comprise unequal numbers of each type of module. The types, configuration, and number of modules may be determined based on the microorganisms in the aqueous culture or the desired product to be produced from the microorganisms. Non-limiting exemplary embodiments of the various module components are described in further detail below.

Figure 2:
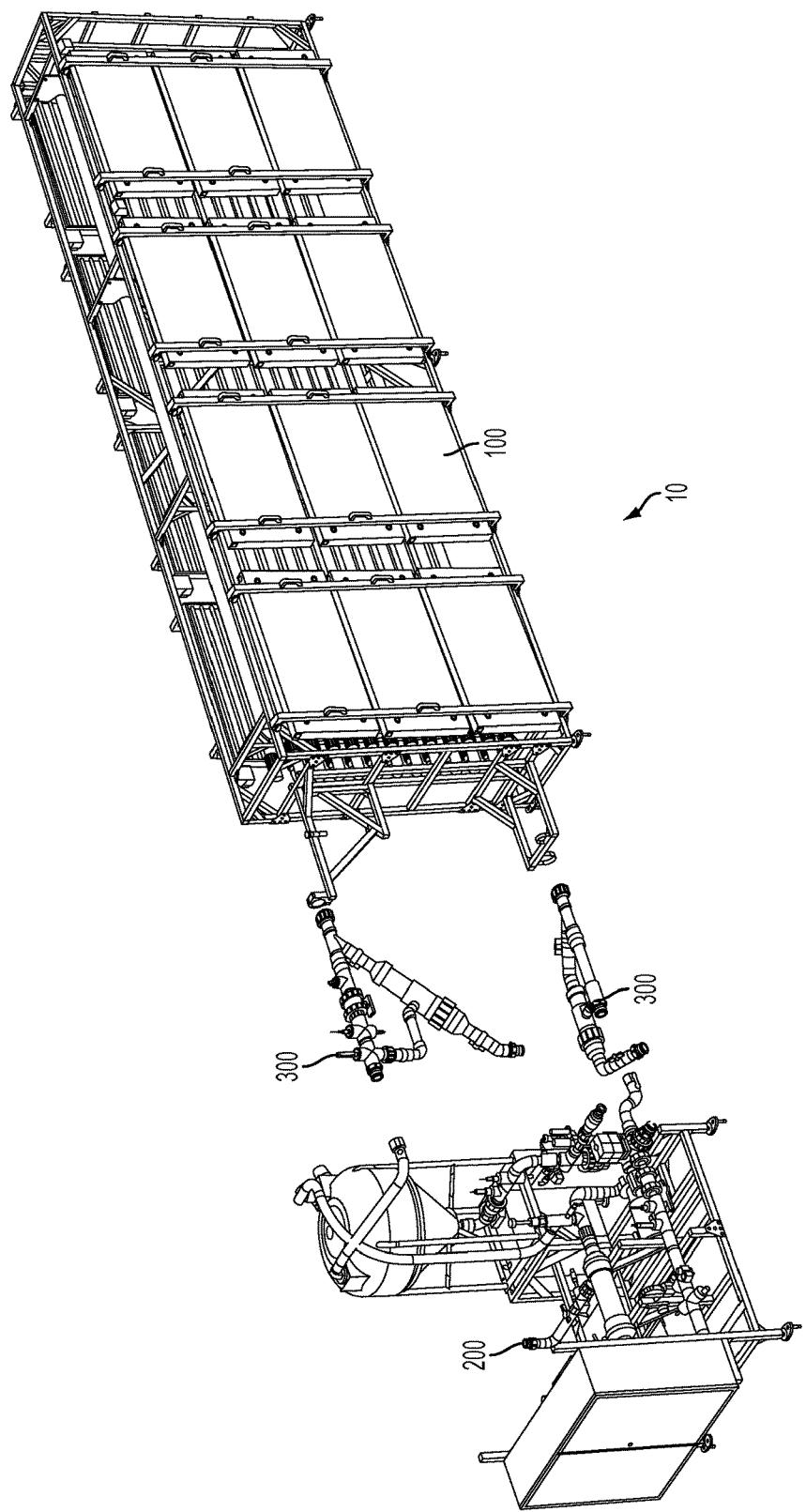
FIG. 2 shows a perspective view of an exemplary modular bioreactor system embodiment with the modules decoupled.

One non-limiting exemplary embodiment of the modular bioreactor system 10 is shown in FIGS. 1-2. FIG. 1 shows a modular bioreactor system 10 with a bioreactor module 100, cleaning module 300, and pump and control module 200 coupled together in fluid communication. FIG. 2 shows a modular bioreactor system 10 with a bioreactor module 100, cleaning module 300, and pump and control module 200 decoupled. All couplers between the modules may comprise quick connection couplers such as, but not limited to cam lock couplers, capable of self-sealing an isolated volume of an aqueous culture medium in each individual module. In some embodiments of the modular bioreactor system, the couplers may comprise traditional couplers such as, but not limited to, threaded connections or bolted together flange connections.

Bioreactor Module

The bioreactor module may comprise any known bioreactor structure capable of culturing an aqueous culture of microorganisms such as, but not limited to, open, closed, raceway pond, tank, bag, trough, flat panel, and tubular bioreactors. An aqueous culture of microorganisms may be circulated through the bioreactor module to facilitate growth of the microorganism. Variables that may dictate the configuration, materials, and components of the bioreactor module may comprise: desired culture conditions, such as phototrophic, mixotrophic, and heterotrophic; a desire to transition between culture conditions; the microorganisms to be cultured; the desired product to be produced from the microorganism culture; and the volume of the aqueous culture. For example, the configuration of a bioreactor module culturing a microorganism monoculture for use in a pharmaceutical product may differ from the configuration of a bioreactor module culturing a microorganism polyculture (e.g., multiple microorganisms in a single culture) to produce lipids for use in a fuel product.

In one non-limiting exemplary embodiment, the bioreactor module comprises a tubular bioreactor module. The tubular bioreactor module may comprise a support frame, and a culture tube or plurality of tubes. For embodiments culturing microorganisms in phototrophic or mixotrophic conditions, the bioreactor module may comprise at least one lighting device, the ability to receive natural light, or both. The support frame may comprise at least one structural frame segment, at least one carrier for the culture tube or plurality of tubes. In some embodiments, the support frame may further comprise elements for mounting at least one lighting device. The at least one structural frame segment and at least one tube carrier may support the culture tube or plurality of tubes in a configuration to optimize the transmission of light to and the utilization of light by the culture of microorganisms within each segment of the culture tube or plurality of tubes. The support frame may comprise any suitable material such as metal, metal alloys, plastics, polymers, polycarbonate, or wood. The frame may be coated with a material that is resistant to environmental elements, including coatings to delay the onset of corrosion from salt water environments. The support frame may comprise both opaque components and components with some degree of transparency or translucency. The elements of the support frame may be joined by any known means such as, but not limited to, welds, bolts, nails, and snap-lock fittings. In some embodiments, the structural frame segments may comprise an extruded metal or metal alloy.

Figure 11:
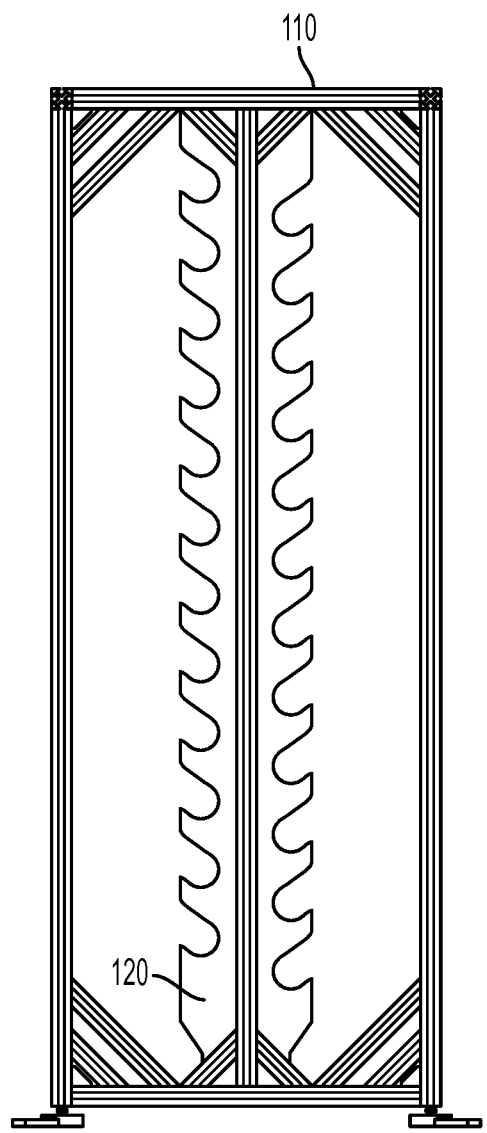
FIG. 11 shows a front view of a carrier for the tube segments and structural frame segments of an exemplary tubular bioreactor module.

One non-limiting exemplary embodiment of a tubular bioreactor module 100 comprising a support frame is shown in FIGS. 3-12. The structural frame segments 110 of the support frame are shown as horizontal, vertical, and angled bars, tubes, and beams. In FIG. 11, the carrier 120 for supporting tube segments is shown. The carrier 120 may be transparent to minimize the blocking of light from the at least one lighting device or natural light source to the culture tube segments 140, 141. The carrier 120 also holds the straight culture tube segments 140 in a horizontally staggered and vertically spaced arrangement on both sides of the carrier in order to optimize the transmission of light form the at least one lighting device or natural light source to the culture tube 140 segments as shown in FIGS. 5, 9-10, & 12. Multiple carriers 120 may be used in a single bioreactor module 100 to support the straight culture tube segments 140.

Figure 3:
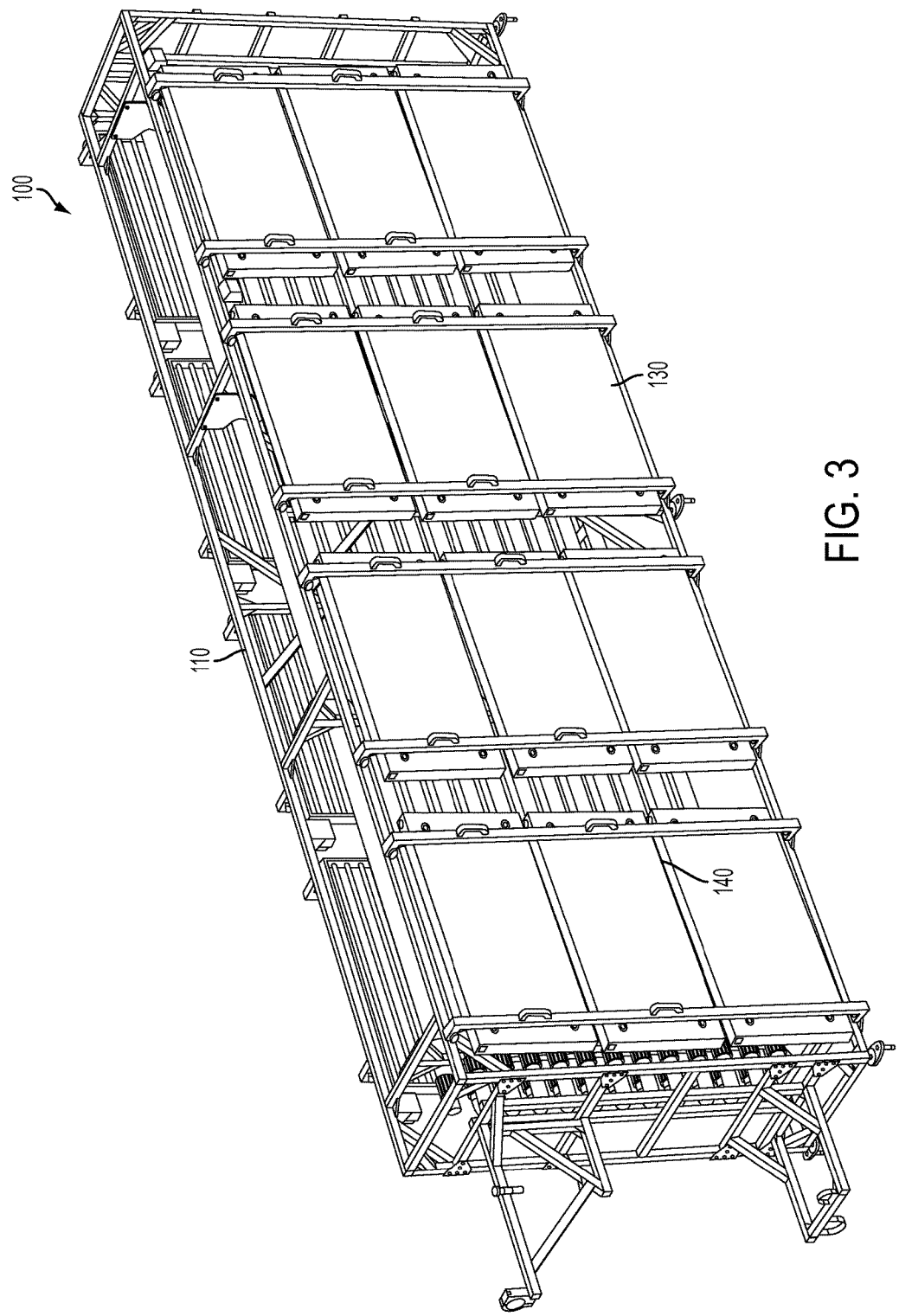
FIG. 3 shows a perspective view of an exemplary tubular bioreactor module embodiment with lighting panels in a closed position.
Figure 4:
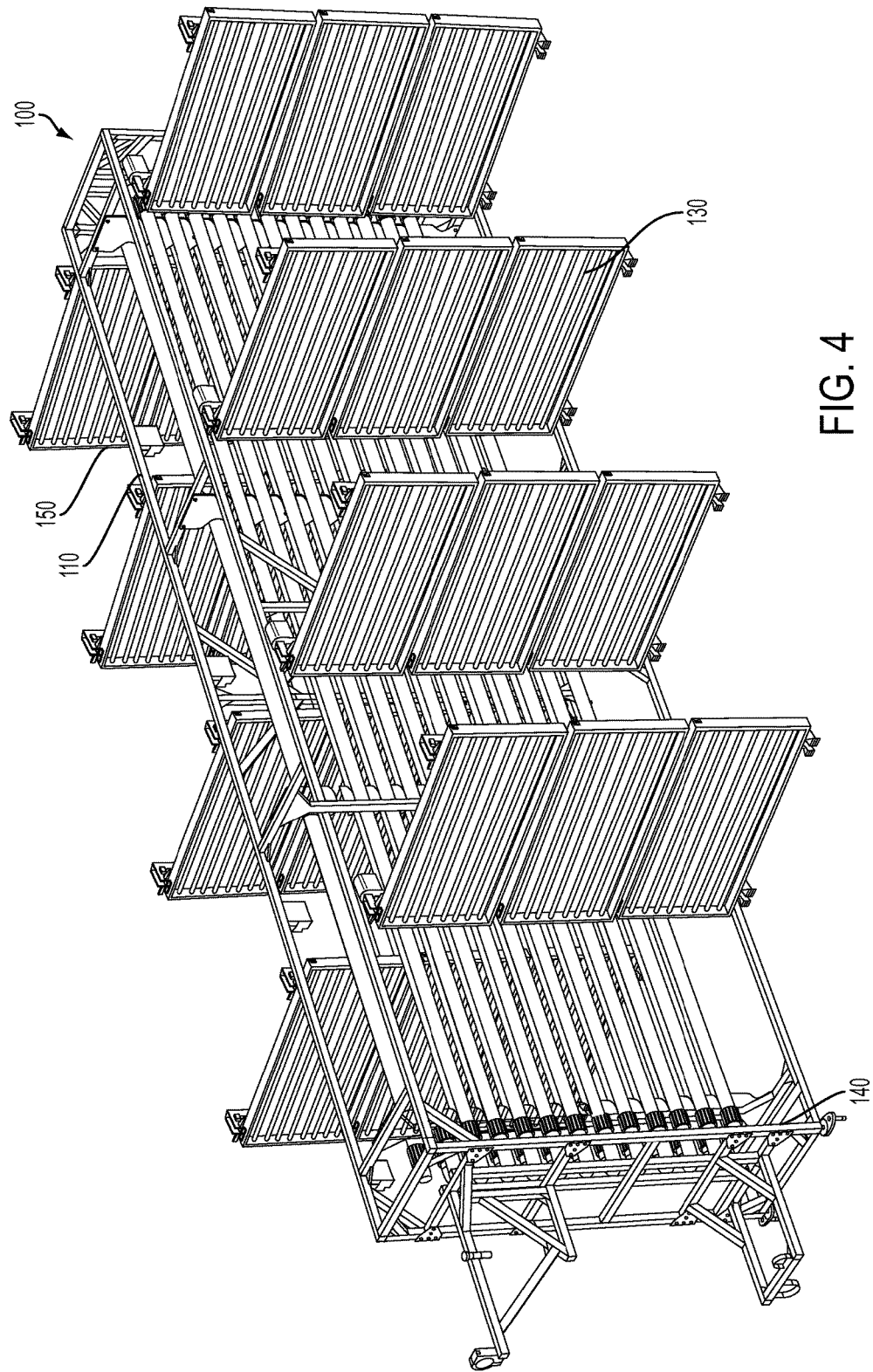
FIG. 4 shows a perspective view of an exemplary tubular bioreactor module embodiment with lighting panels in an open position.
Figure 5:
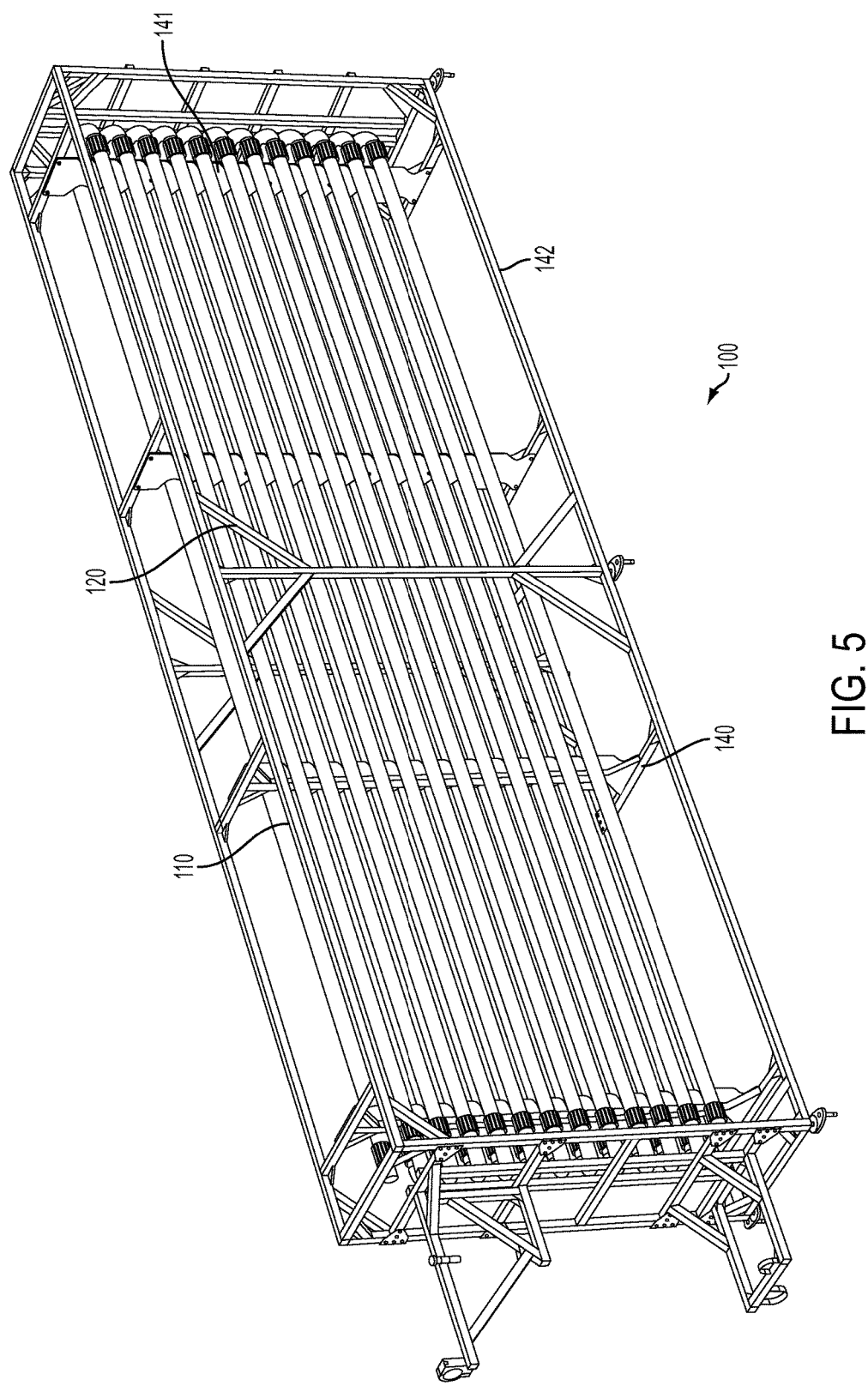
FIG. 5 shows a perspective view of an exemplary tubular bioreactor module embodiment.
Figure 6:
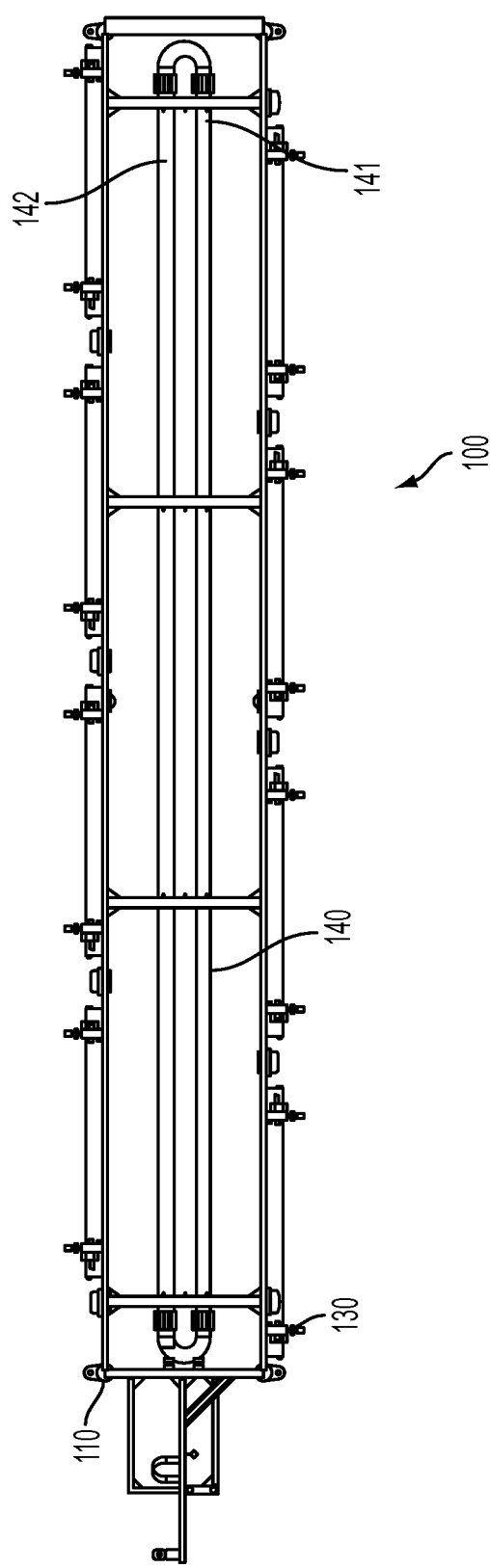
FIG. 6 shows a top view of an exemplary tubular bioreactor module embodiment.
Figure 7:
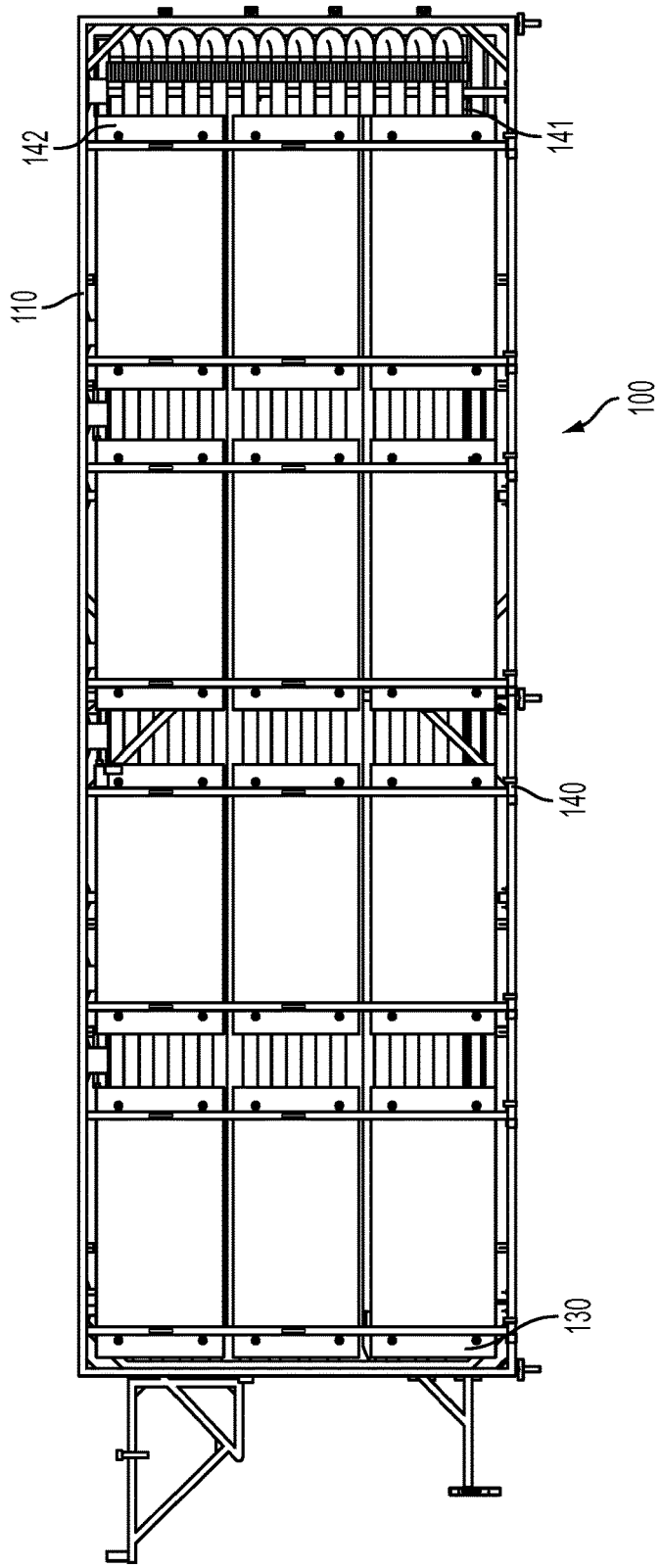
FIG. 7 shows a side view of an exemplary tubular bioreactor module embodiment with lighting panels in a closed position.
Figure 8:
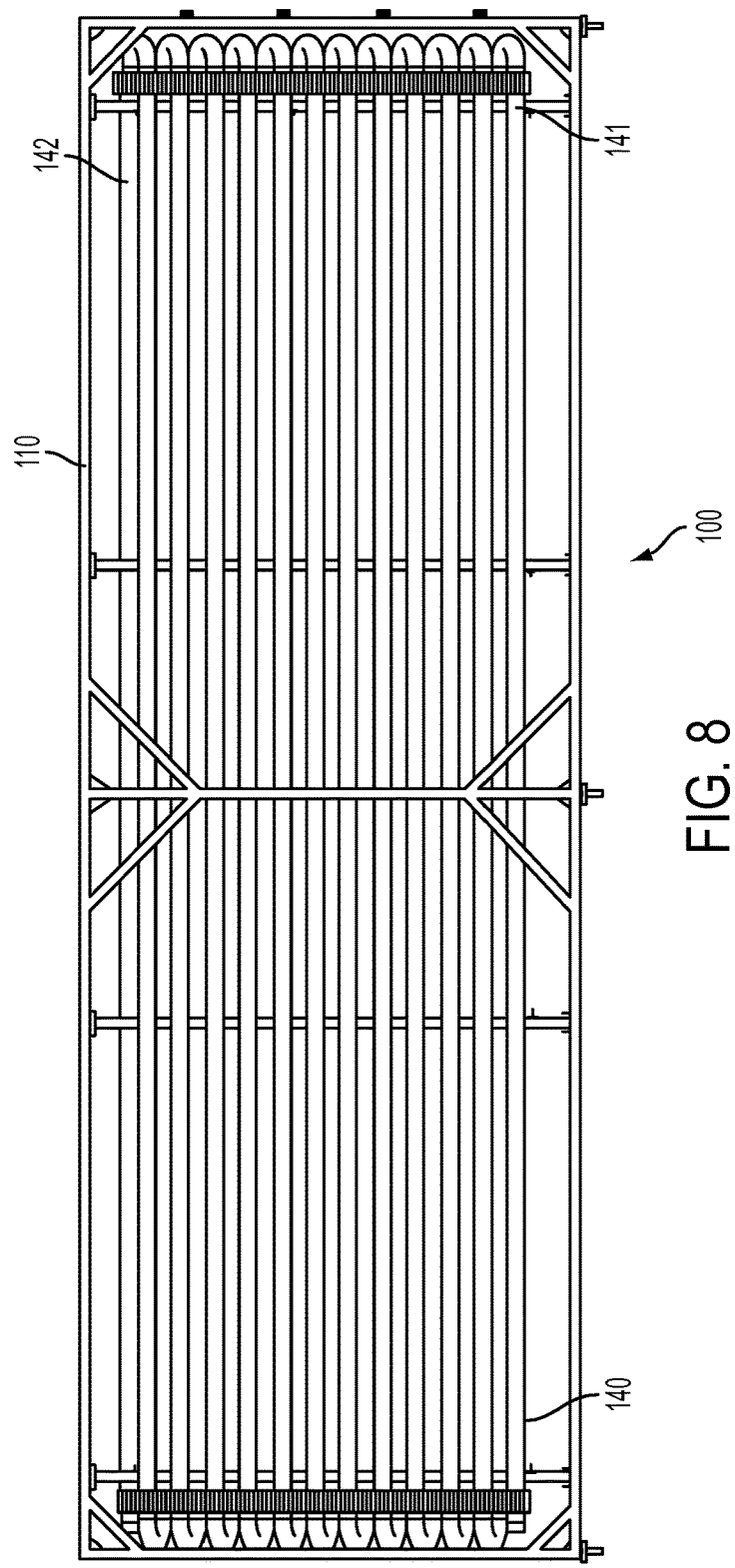
FIG. 8 shows a side view of an exemplary tubular bioreactor module embodiment.
Figure 12:
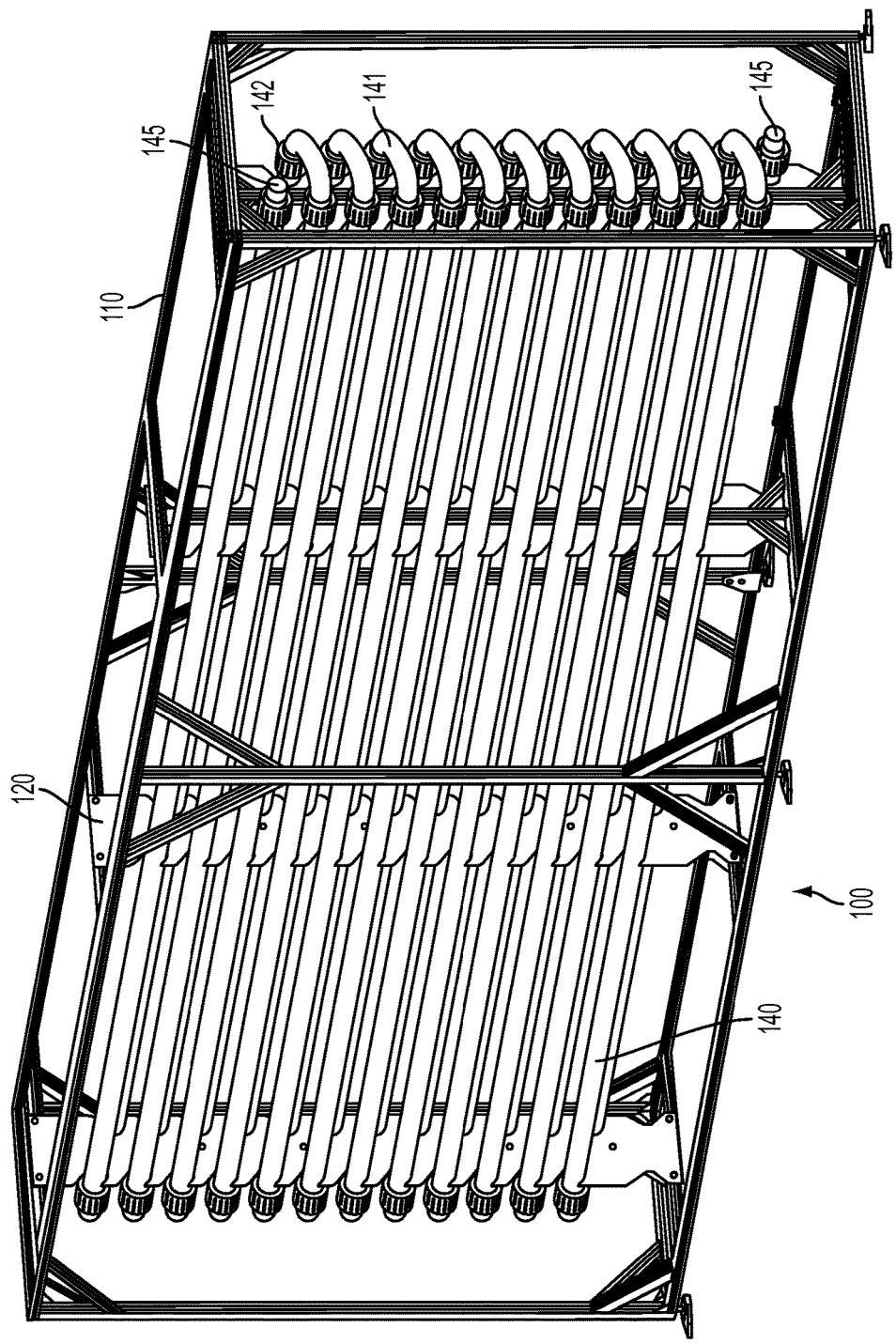
FIG. 12 shows a perspective view of a carrier loaded with tube segments and the structural frame segments of an exemplary tubular bioreactor module.

In FIGS. 3-4, swiveling panels 130 for mounting lighting devices 150 are shown in both the closed and open positions. The panels 130, may be coupled to the structural frame segments 110 with any known pivoting member, such as a hinge. With the panels 130 in the open position, the lighting devices 150 may be easily accessible for repair, replacement, or reconfiguration. Additionally, with the panels 130 in the open position, easy access may be provided to the culture tube segments 140. The swiveling panels 130 may comprise lighting devices 150 mounted on the panels 130 in any desired configuration to optimally transmit light from the at least one lighting device to the culture tube segments 140, 141 when the panels 130 are in the closed position. In an embodiment utilizing heterotrophic culture conditions only, the panels 130 may not comprise mounted lighting devices but instead may be utilized to block the transmission of external light to the culture tube segments 140, 141. FIGS. 5, 8 & 12 show a tubular bioreactor module 100 embodiment without panels or lighting devices in which the bioreactor module 100 may receive natural light (e.g., sunlight), ambient light from an indirect artificial light source (e.g., overhead light when the bioreactor is housed in a larger building), or no light at all (e.g., outdoors at night, inside a building with no artificial light).

The culture tube or plurality of culture tubes of the bioreactor module may comprise: a single tube; plurality of straight and/or bending culture tube segments coupled in series to produce a single tubular path; a plurality of tube segments producing a plurality of tubular paths connected in parallel; or any combination thereof. The flow path formed by the culture tube or plurality of culture tubes may comprise a straight, serpentine, winding, helical, spiral, or curved flow path. The culture tube segments may comprise material which is opaque, transparent, or any degree of partial transparency. The culture tube segments may have a cross section of any shape such as, but not limited to, circular, oval, rounded, obround, square, rectangular, and polygonal. The thickness of the culture tube walls may be selected based on desired light transmission or refraction properties, thermal properties, and structural integrity. The culture tube segments may a have cross sectional area and length of any size, and may be selected based on a desired light path, desired capacity, available space, and capability of a pump and control module.

Culture tubular materials may comprise glass, plastic, polymers, polyvinyl chloride (PVC), metal, silicone, and metal alloys. In some embodiments, a film or coating may be applied to a surface of the culture tube or plurality of tubes to selectively allow the transmission of light in certain wavelength spectrums and block or reflect transmission of light other wavelength spectrums. The culture tubular material may be selected based on weight, culture conditions, light transmissibility, biofouling resistance, cleaning methods utilized, resistance to scratching, and resistance to hazing. The culture tube segments may be coupled by any connector known in the art to join ends of tubes for sealed fluid communication. The connectors may be removable and reusable. The ends of the culture tubes may comprise straight ends, threaded ends, flanged ends, or ends comprising beads or other protrusions.

In some embodiments, the culture tube diameters, spacing, and configuration may be selected to optimize the transmission of the light from the at least one lighting device to the culture of microorganism. In some embodiments, the culture tube segments may all have the same diameter. In some embodiments, the culture tube segments may have different diameters. In some embodiments, the culture tube or plurality of tubes may have interior surface features such as, but not limited to, baffles to create turbulence within the aqueous culture medium flowing through the culture tube or plurality of tubes. In some embodiments, the inlet culture tube segment and the outlet culture tube segment of a tubular bioreactor module may comprise quick connect couplers, such as cam lock couplers, for coupling the bioreactor module to other modules, such as additional bioreactor modules, pump and control modules, and cleaning modules.

Figure 9:
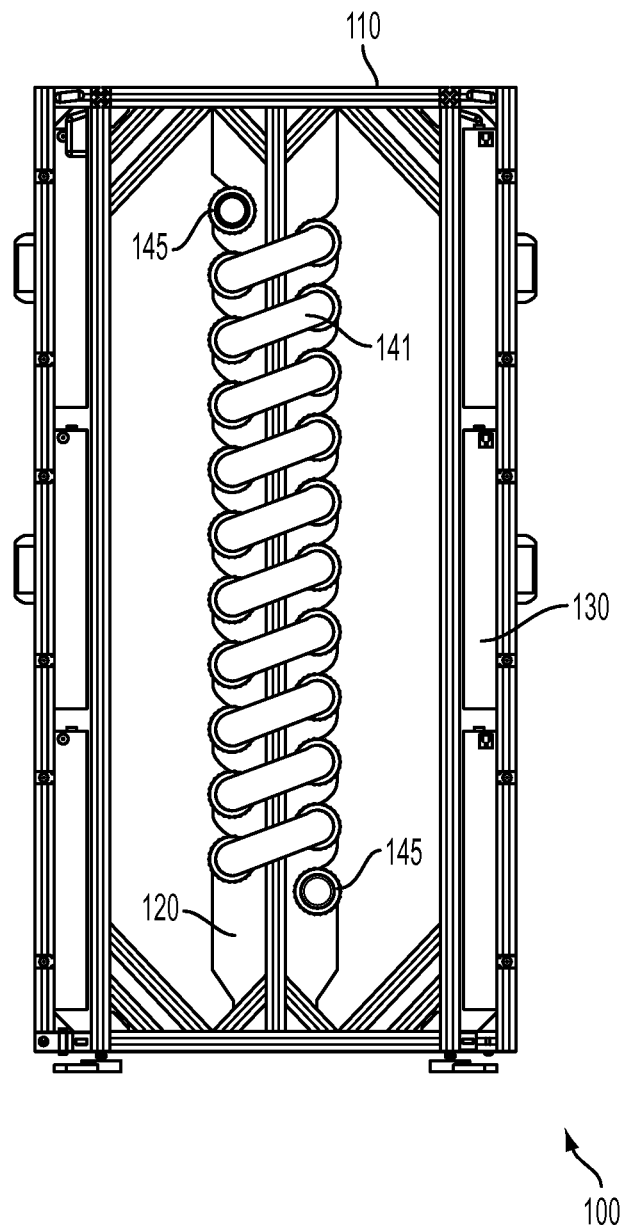
FIG. 9 shows a front view of an exemplary tubular bioreactor module embodiment.
Figure 10:
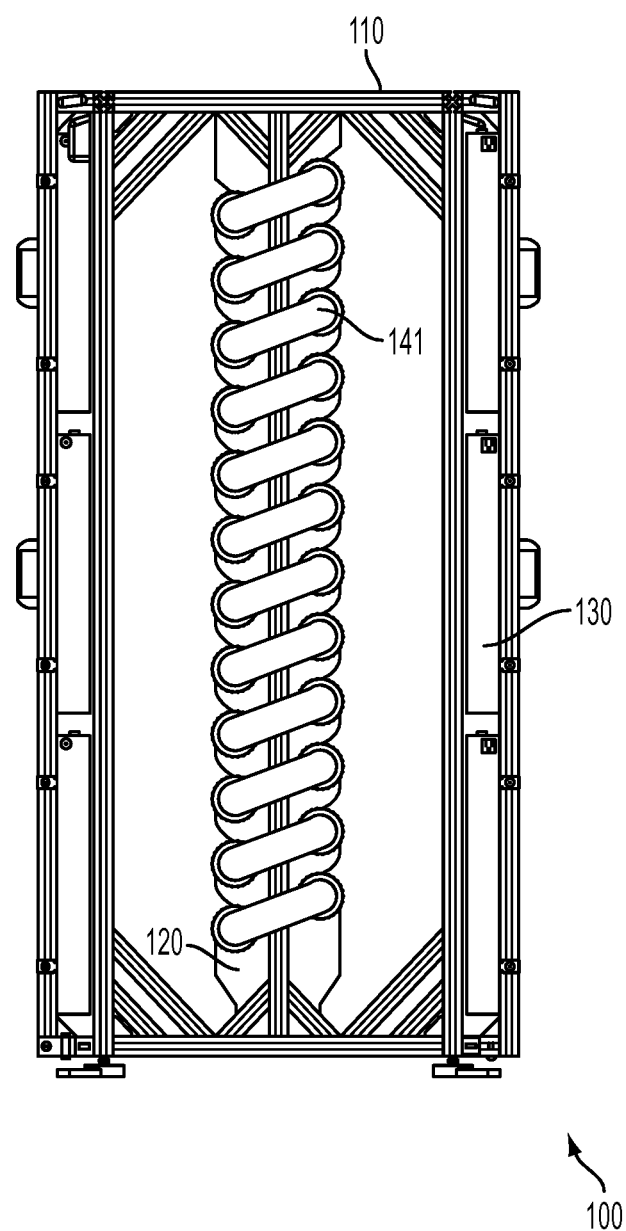
FIG. 10 shows a back view of an exemplary tubular bioreactor module embodiment.
Figure 13:
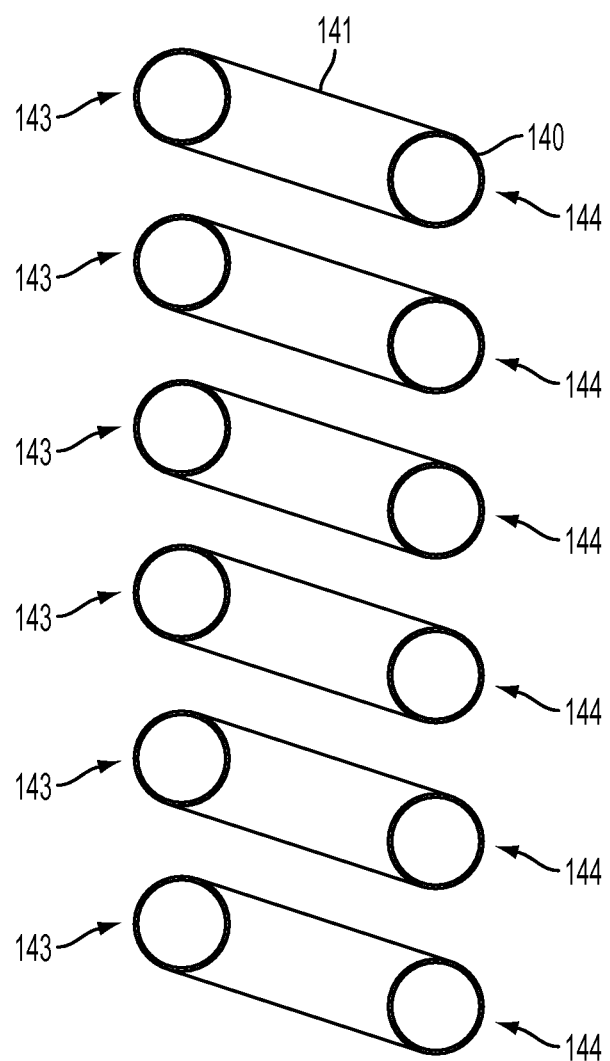
FIG. 13 shows a cross-sectional view of the connected tubular segments in an exemplary vertically spaced and horizontally staggered arrangement.
Figure 14:
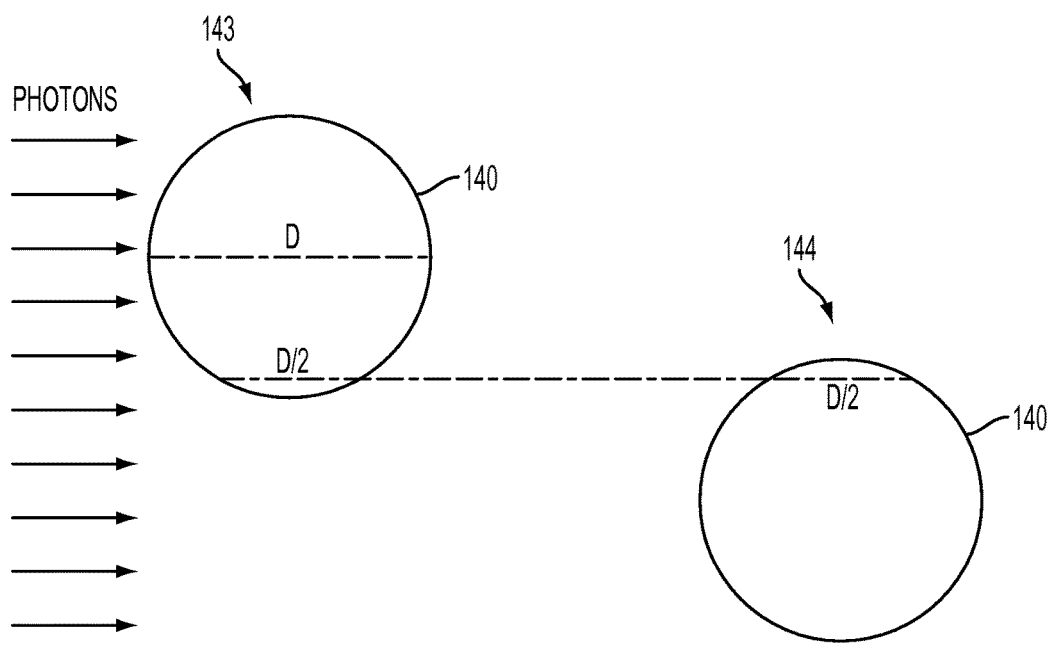
FIG. 14 shows the light path along a horizontal plane in a cross-sectional view of the connected tubular segments in an exemplary vertically spaced and horizontally staggered arrangement.
Figure 15:
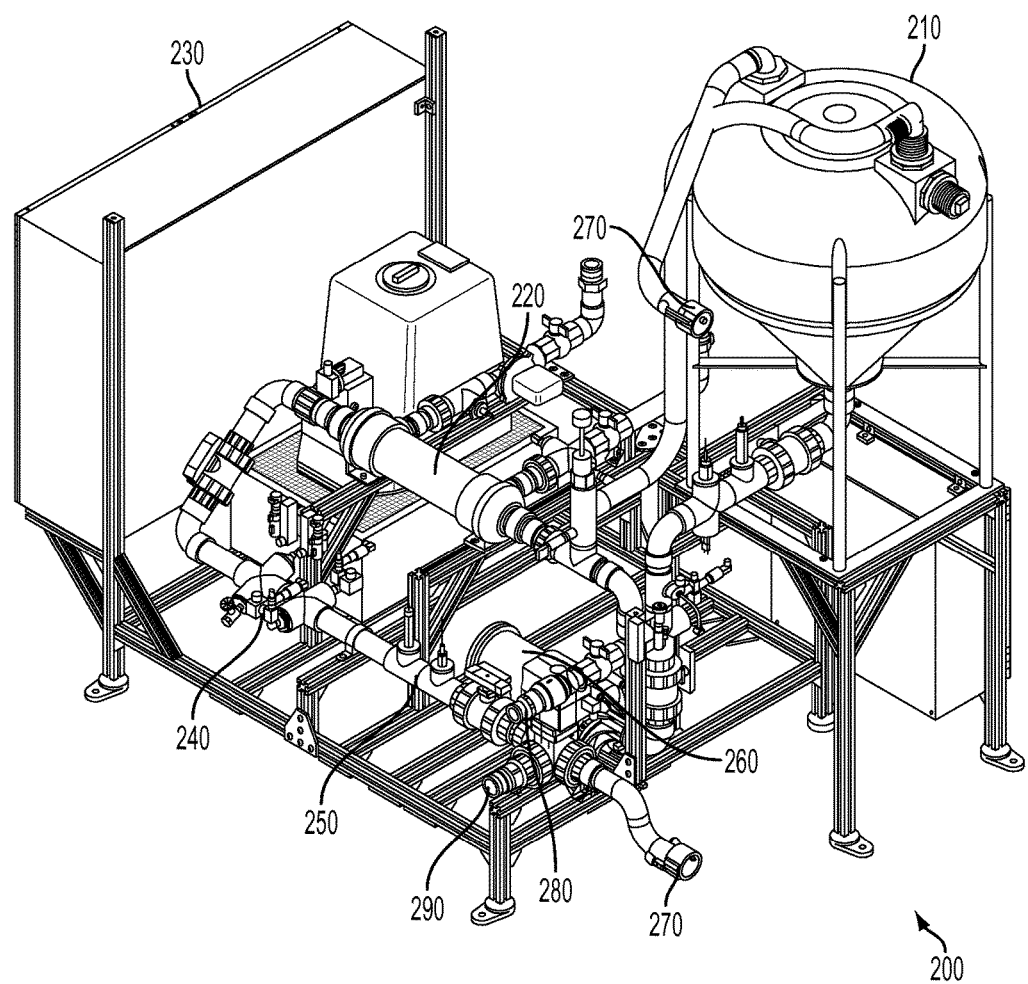
FIG. 15 shows a perspective view of an exemplary pump and control module embodiment.
Figure 16:
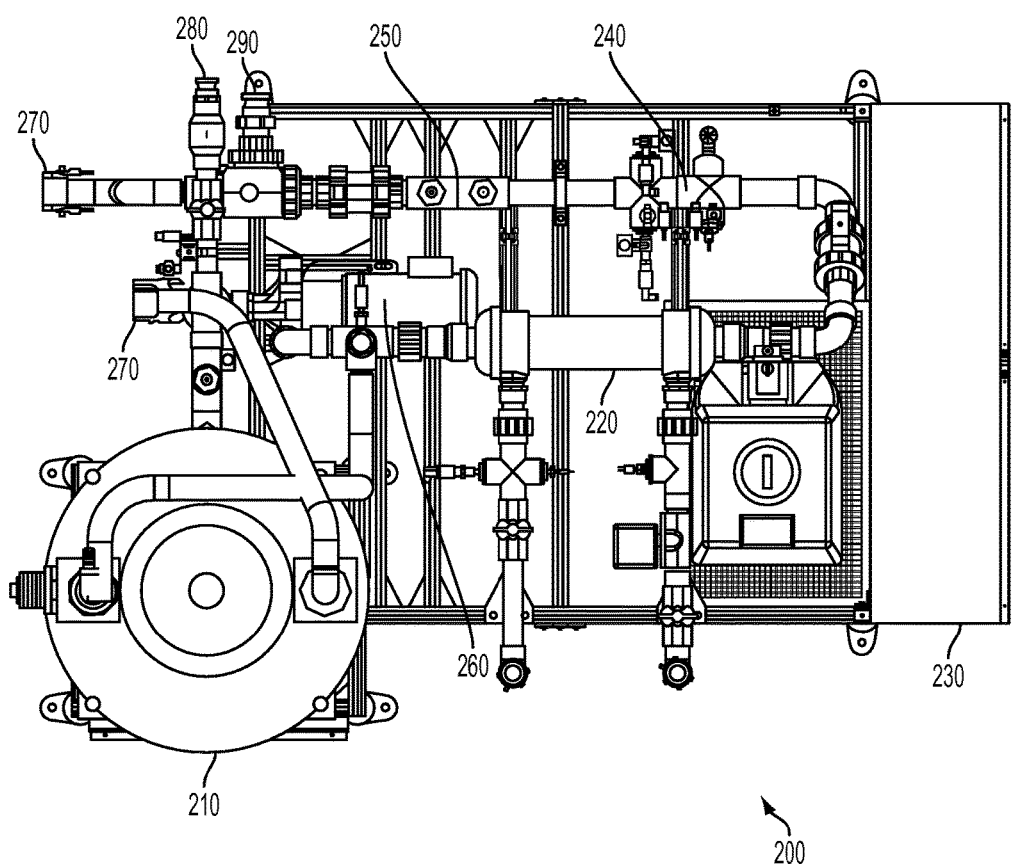
FIG. 16 shows a top view of an exemplary pump and control module embodiment.
Figure 17:
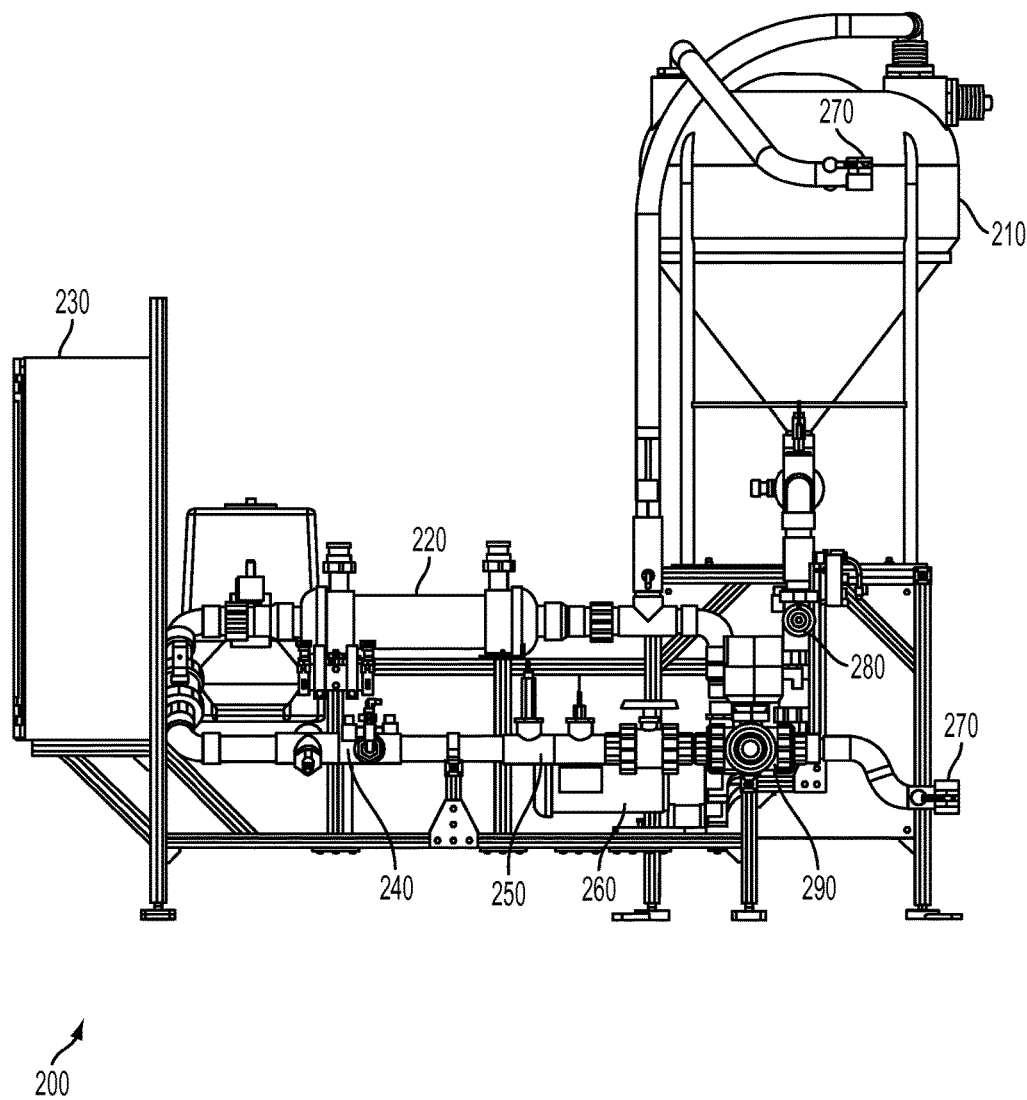
FIG. 17 shows a right side view of an exemplary pump and control module embodiment.
Figure 18:
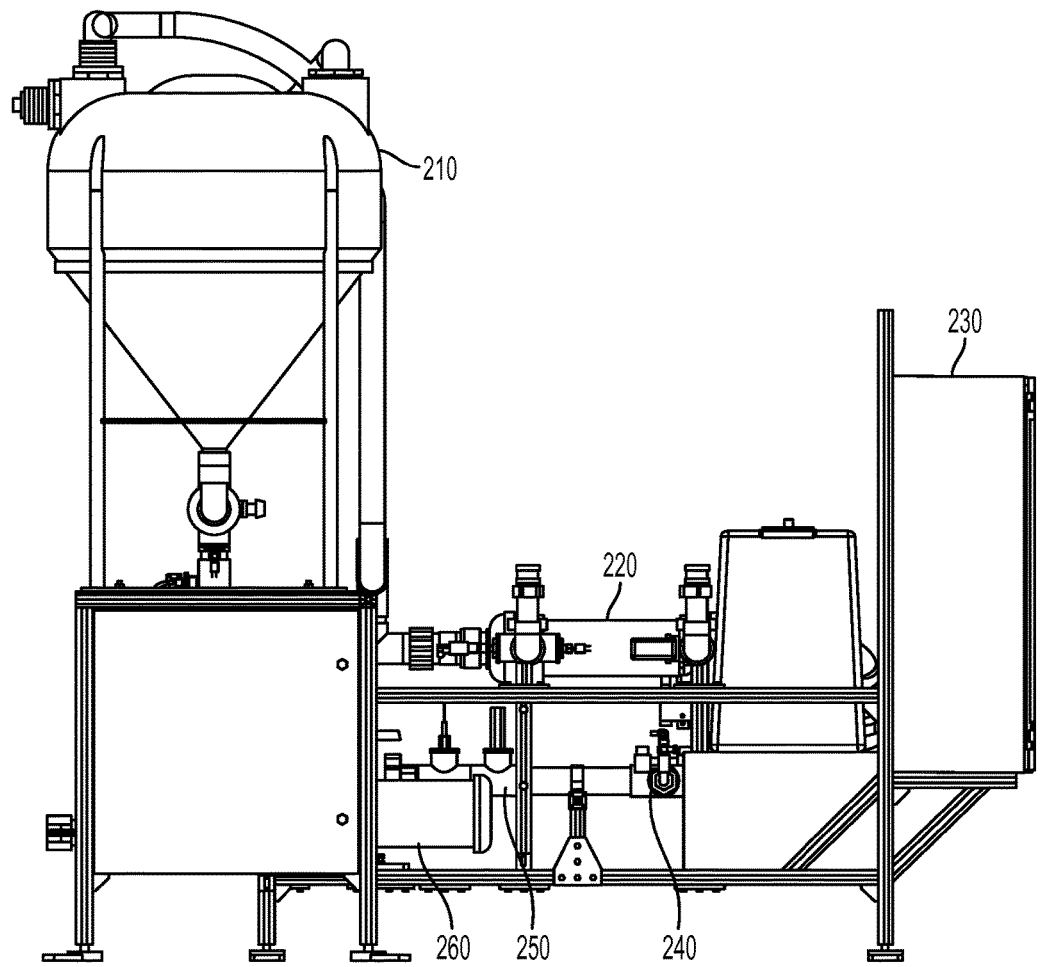
FIG. 18 shows a left side view of an exemplary pump and control module embodiment.
Figure 19:
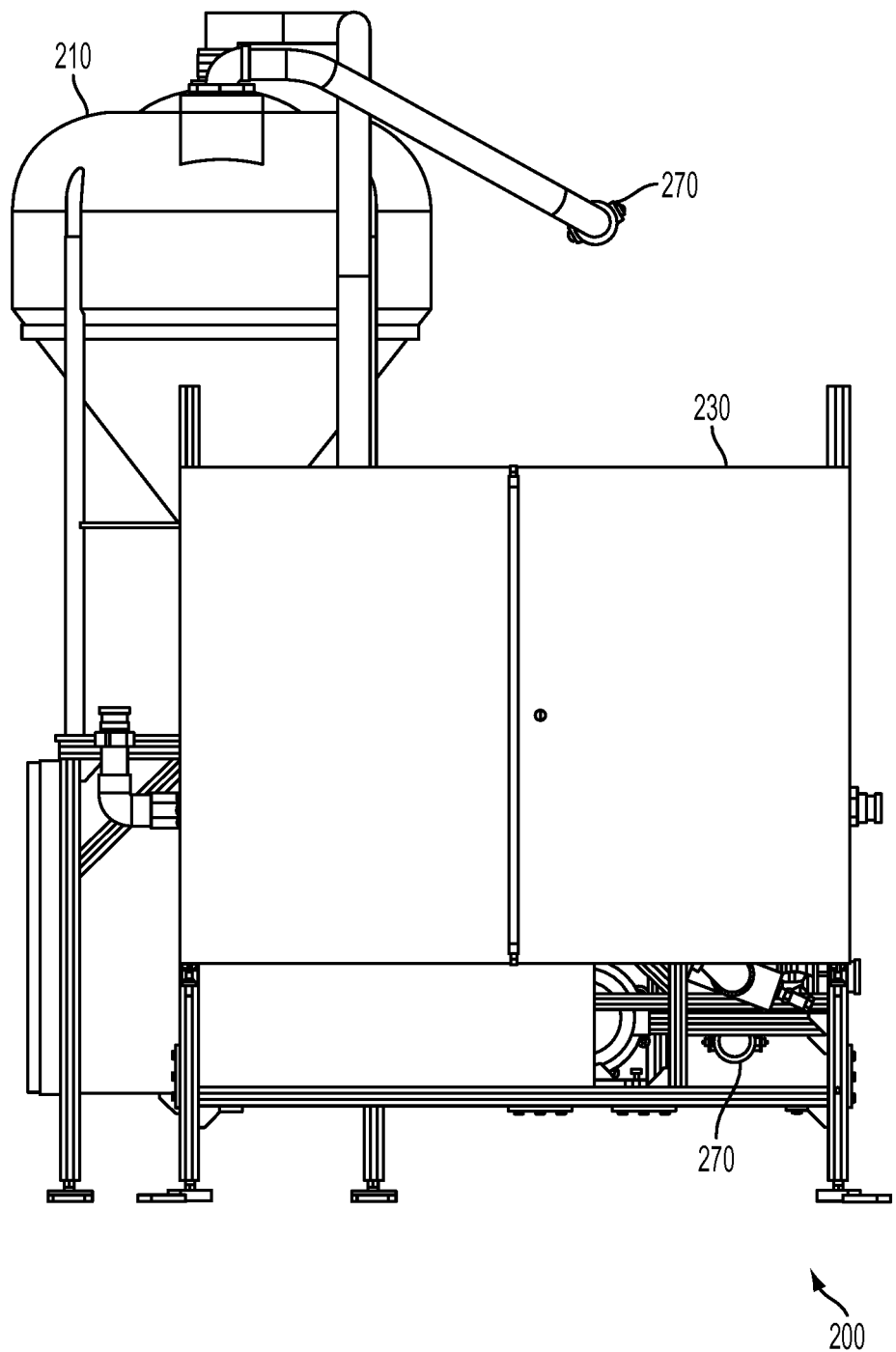
FIG. 19 shows a front view of an exemplary pump and control module embodiment.
Figure 20:
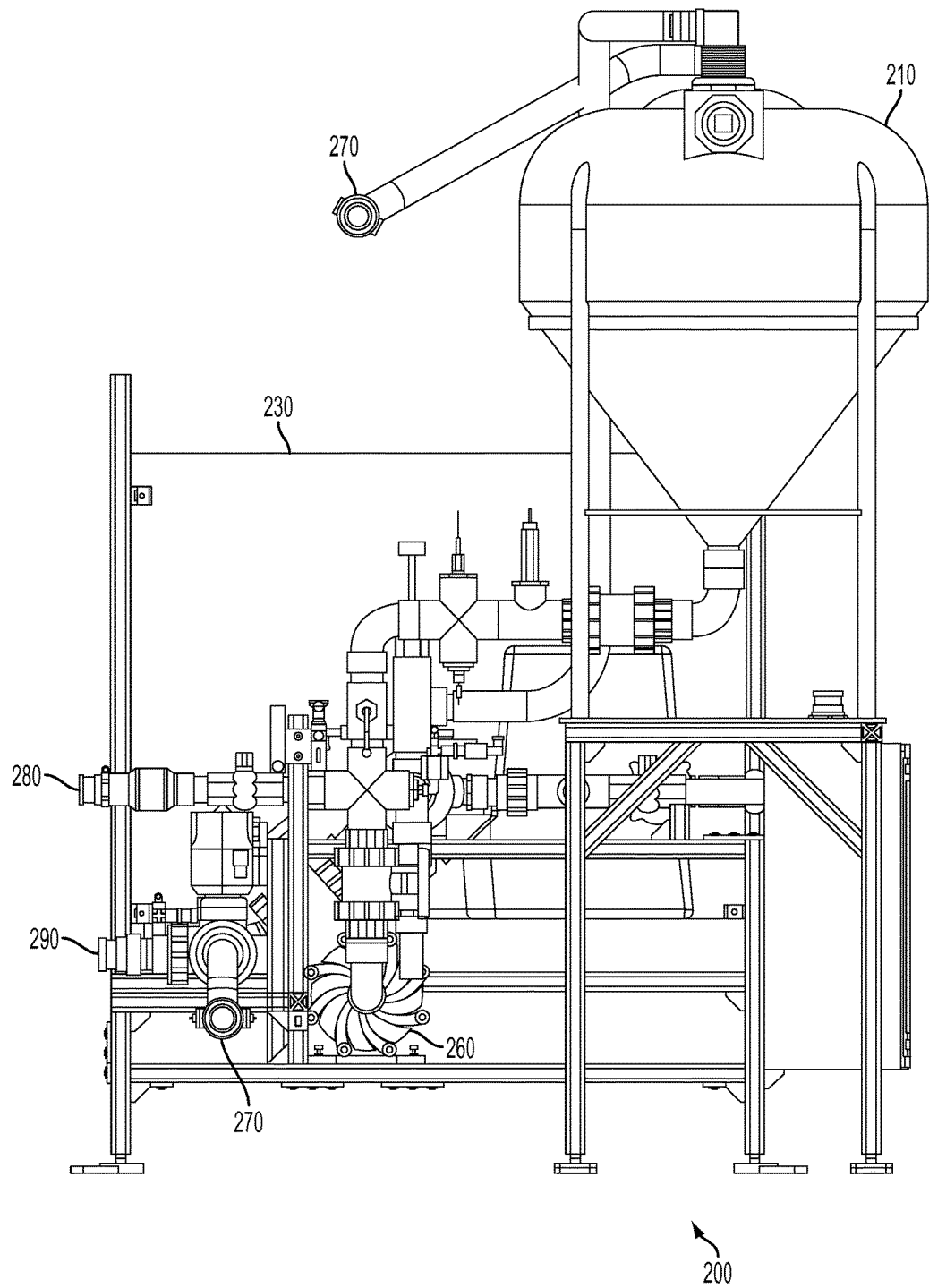
FIG. 20 shows a back view of an exemplary pump and control module embodiment.

One non-limiting exemplary embodiment of a plurality of culture tube segments coupled together to form a singular tubular flow path for a tubular bioreactor module is shown in FIGS. 3-10 & 12-14. As shown in FIGS. 8-10 & 12, a plurality of straight culture tube segments 140 and a plurality of U-bend culture tube segments 141 are coupled together by connectors 142 to form a single helical tubular flow path for an aqueous culture of microorganisms. As shown in FIG. 12-13, the straight culture tube segments 140 are supported by a carrier 120 disposed horizontally between two arrays of culture tube segments 140, one on each side of the carrier 120. The support provided by the carrier 120 horizontally staggers the culture tube segments 140 and equally spaces in a vertical manner the culture tube segments 140 in both the first array 143 and the second array 144. As shown in FIGS. 9 and 12, the inlet culture tube segment and the outlet culture tube segment of a tubular bioreactor module may comprise a quick connect couplers 145, such as cam lock couplers, for coupling the bioreactor module to other modules, such as additional bioreactor modules, pump and control modules, or cleaning modules, and sealing an isolated volume of aqueous culture in the bioreactor module when decoupled from other modules.

In FIGS. 8-10 & 13-14, the vertical spacing of the culture tube segments 140 and horizontal staggering of the first array 143 and second array 144 is shown in more detail. The cross section view of the culture tube segments 140 in relation to the transmission of light on a horizontal plane shows how the vertical spacing and horizontal staggering optimizes the configuration of culture tube segments 140 for the receipt of light by the culture of microorganisms within the inner volume of the culture tube segments 140.

Each of the tube segments 140 has a longitudinal axis running along the length of the tube segment. As shown in the diagram in FIG. 14, the vertical spacing and horizontal staggering configuration of the tube segments 140 allows the transmission of light along a horizontal plane intersecting the cross-sections of the culture tube segments 140 in a direction normal to the longitudinal axis of the culture tube segments 140 to travel a light path through the interior volume of the culture tube segments 140 less than or equal to the diameter (D) of the culture tube. Along any particular horizontal plane intersecting the cross-sections of the culture tube segments 140 at a direction normal to the longitudinal axis for the portions of the culture tube segment 140 in the first array 143 with a horizontal distance between D and D/2, there is no overlap with a portion of the culture tube segment 140 in the second array 144. Along any particular horizontal plane intersecting the cross-sections of the culture tube segments 140 at a direction normal to the longitudinal axis for the portions of the culture tube segment 140 in the first array 143 with a horizontal distance less than D/2, there is only overlapping of portions of the culture tube segment 140 in the second array 144 with a horizontal distance which is also less than D/2. Therefore, the vertical spacing and horizontal staggering configuration of the culture tube segments in the first array 143 and the second array 144 allows light traveling on any horizontal plane at a direction normal to the longitudinal axis for the portions of the culture tube segment 140 to transmit a total distance less than or equal to D through the interior volume of the culture tube segments. As shown in FIG. 13, this overlapping pattern may be repeated in the vertical arrays 143, 144 of culture tube segments 140 to create a tubular bioreactor module of any height, volume, and flow path length.

While the vertically spaced and horizontally staggered arrangement ensures that light on a horizontal plane at a direction normal to the longitudinal axis of the culture tube 140 will travel a distance less than or equal to D through the interior volume of the culture tubes 140, the slight overlapping also ensures that all light (100%) on a horizontal plane at a direction normal to the longitudinal axis of the culture tube 140 may strike a culture tube 140 in a uniform manner and may not be wasted by passing through the bioreactor module or striking a surface other than the culture tube surface. Another benefit of the vertical spacing and horizontal staggering configuration is a large surface area of the culture tube segments may also exposed to light traveling on non-horizontal planes, such as planes at angles between 1-90 degrees, as well as light which is reflected off of other culture tube segment 140 surfaces. The vertical spacing and horizontal staggering arrangement of the culture tube segments may be repeated in the first 143 and second 144 array to produce the helical tubular path shown, and also provides a space efficient configuration with a small footprint for efficiently utilizing vertical space. The vertically spaced and horizontally staggered arrangement of the culture tube segments may be further refined by factoring light emission angles, reflection, and refraction for specific lighting devices and culture tube materials. Additionally, while the vertically spaced and horizontally staggered arrangement is discussed in the context of an embodiment with multiple tube segments connected in series in a single flow path, the vertically spaced and horizontally staggered arrangement may also be utilized in an embodiment with separate tube segments that comprise separate flow paths, and in combinations of connected and separate flow paths. In some embodiments, the vertically spaced and horizontally staggered arrangement may also be used with tube segments with non-circular cross sections.

The at least one lighting device may comprise any lighting device capable of providing light to a culture of microorganisms such as, but not limited to, fluorescent tubes, light emitting diodes (LED), micro LEDs, high pressure sodium lamps, high intensity discharge lamps, neon lamps, metal vapor lamps, halogen lamps, sulfur plasma lamps, and incandescent bulbs. In some embodiments, the at least one lighting device may be selected or tuned to provide light of a particular wavelength spectrum or combination of spectrums such as, but not limited to, violet (about 380-450 nm), blue (about 450-495 nm), green (about 495-570 nm), yellow (about 570-590 nm), orange (about 590-620 nm), red (about 620-750 nm), and far red (about 700-800 nm), infrared (IR) (about 1,000-20,000 nm) and ultraviolet (UV) (about 10-400 nm). In some embodiments, the application of light may be continuous, discontinuous, flashing, or pulsing to create any desired light/dark cycle. In some embodiments, the intensity of light supplied by the at least one lighting device may comprise a constant intensity or variable intensity. The at least one lighting device may be mounted anywhere on the bioreactor module, or may be separate from the bioreactor module. In one non-limiting exemplary embodiment, FIG. 4 shows a plurality of lighting devices 150 mounted on panels 130 to apply light to the culture tube segments 140 when the panels 130 are in the closed position shown in FIG. 3.

In some embodiments, the at least one light device may be provided on one side of the bioreactor module, and a second side of the bioreactor module may have no lighting devices or may have the panels with lighting devices pivoted open. In one non-limiting exemplary embodiment a modular bioreactor system with lighting devices on a first side and an open second side is shown in FIG. 30. The modular bioreactor system comprises a pump and control module 200 and a bioreactor module 100. The bioreactor module 100 has lighting devices 150 on a first side, and the second side is open and facing the sun 800 which provides natural sunlight 810 to the open side. In some embodiments, lighting devices may be added to the open second side at night or when natural sunlight is unavailable.

In some embodiments, the pressure in a bioreactor module comprising straight culture tube segments coupled to bending culture tube segments, such as U-bends, may result in the straight and bending culture tube segments separating enough to cause leakage of the aqueous culture. To prevent leakage, a bioreactor module may comprise a retention device utilizing a tension force to maintain a liquid tight seal at the tube segment couplings.

Figure 26:
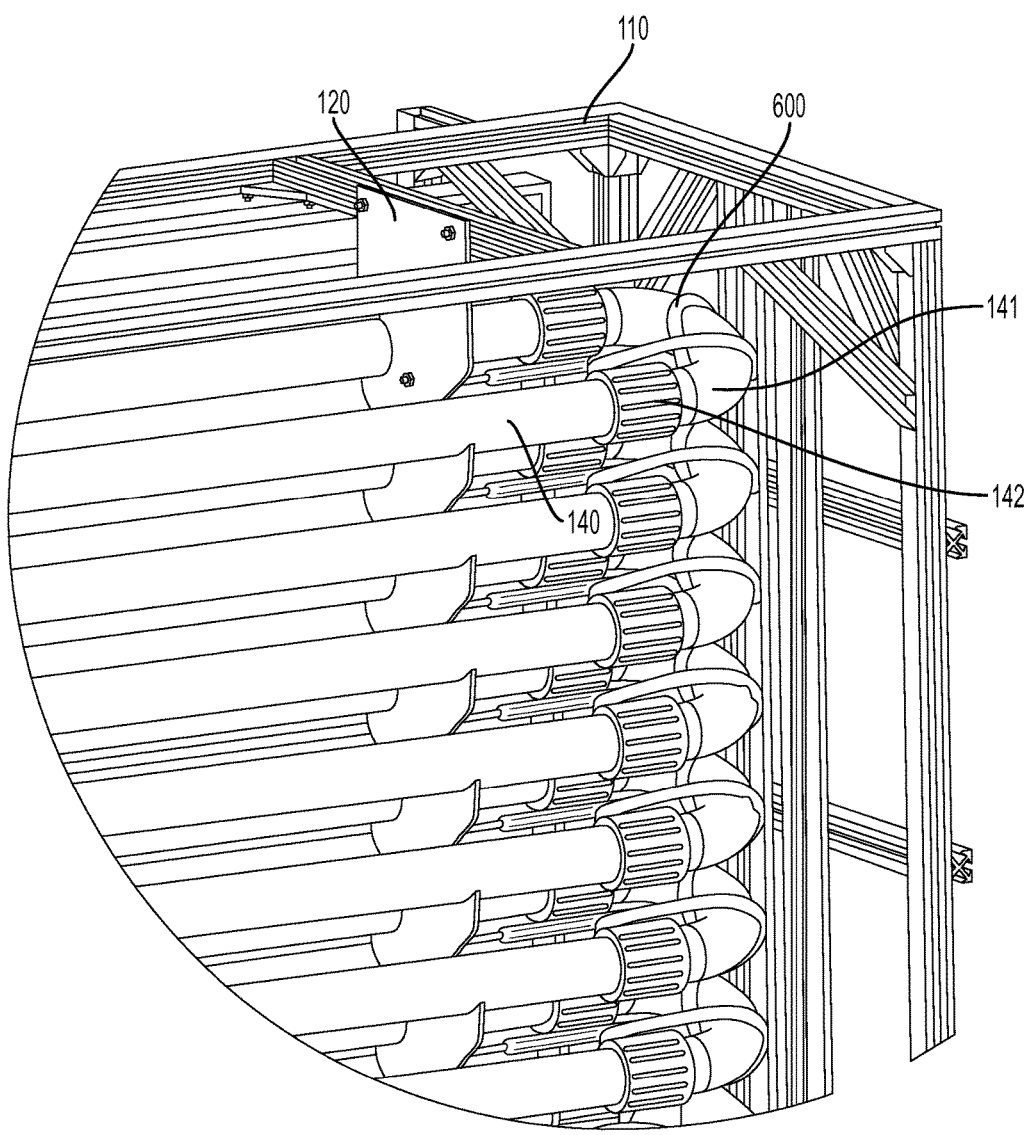
FIG. 26 shows a perspective view of an exemplary retention device embodiment engaged on a tubular bioreactor module.
Figure 27:
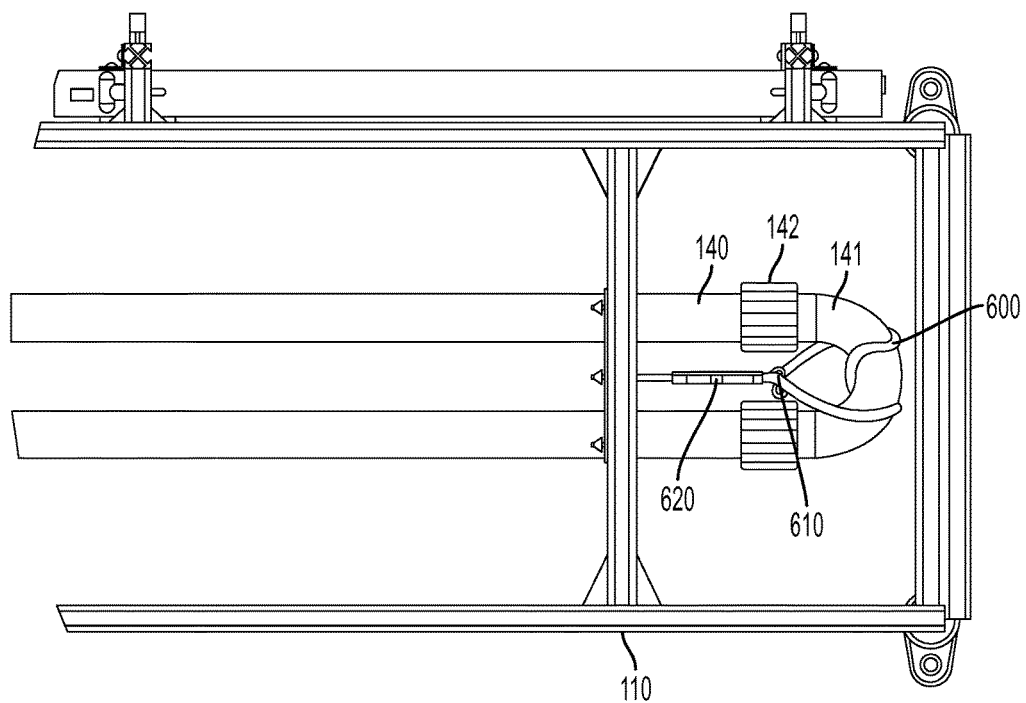
FIG. 27 shows a top view of an exemplary retention device embodiment engaged on a tubular bioreactor module.

One non-limiting exemplary embodiment of a retention device is shown in FIGS. 26-27. The device comprises a flexible strap 600 wrapped around the U-bend culture tube segment 141. The flexible strap 600 may be fabric, nylon, rubber, or any other suitable elastomeric material. The flexible strap 600 may be opaque, transparent, or any degree of transparency. The flexible strap 600 may be attached to a turnbuckle 620 by a grommet 610. The turnbuckle 620 may be attached to the support frame of the bioreactor module at the carrier 120 or structural frame elements 110. The tension force on the culture tube segments 140, 141 and connector 142 may be adjusted through the turnbuckle 620.

Pump and Control Module

The pump and control module is in direct or indirect fluid communication with the bioreactor module, and may comprise at least one component known in the art for circulating fluid, sensing culture parameters, heat exchange, gas exchange, monitoring culture parameters, nutrient addition, removing water, controlling contamination, and automated control with an aqueous culture of microorganisms, arranged in any usable configuration. In further embodiments, the pump and control module may facilitate the addition of culture media, transfer of culture inoculum, and culture harvest. In some embodiments, a pump uses pressure to circulate the aqueous culture medium through the modular bioreactor system. In some embodiments, a pump may work in combination with gravity, an airlift system, or a water wheel to circulate the aqueous culture medium. A pump may be selected based on power requirements, shear sensitivity of the microorganisms, and space requirements.

In some embodiments, the sensors may be used to monitor and detect parameters of the aqueous culture of microorganisms and operation of the modular bioreactor system. The sensors may comprise photopigment (e.g., chlorophyll), dissolved carbon dioxide, dissolved oxygen, pH, turbidity, flow rate, and temperature sensors. The sensors may be disposed within the flow path of the culture medium at any location along the flow path as the culture medium flows through the pump and control module. In further embodiments, the sensors may comprise optical, ultrasonic, and noise/sound (e.g., to detect pump failure, leaks, or tube breakage) sensors.

In some embodiments, the sensors may be disposed in an isolation mount. The insolation mount may hold the sensor in a mount with a gate that may close a sensor port to isolate the sensor from the aqueous culture. When the gate is in an open position, the sensor may be submerged in the flow the aqueous culture through the sensor port. When the gate is in a closed position, the sensor may be removed from the sensor mount without exposing the aqueous culture to the environment or outside contamination. With the gate closed, the sensor may be removed for cleaning, calibration, inspection, or replacement.

In some embodiments, the heat exchanger may comprise a coil or plate submerged in the flow path of the aqueous culture. The coil or plate may circulate a heat exchange fluid such as chilled water or heated water. In some embodiments the heat exchanger may be disposed within a de-gassing tank, or disposed in a segment of a tube circulating the aqueous culture medium separate from a de-gassing tank. In some embodiments, the heat exchanger for the module bioreactor system may comprise: spraying water on the exterior surfaces of the bioreactor module; controlling the temperature of the environment surrounding the bioreactor module, such as through a heating ventilation and air conditioning (HVAC) unit; passive cooling with forced air circulation; or any combination thereof.

In some embodiments, gas may be removed from the aqueous culture medium through the use of a de-gas tank configured to allow gas in the aqueous culture medium to diffuse from the aqueous culture medium into the air space above the liquid gas interface. In some embodiments, gas may be added to the aqueous culture medium through the injection of gases such as, but not limited to, carbon dioxide, oxygen, air, and nitrogen. In some embodiments, the gas removed from the aqueous culture medium may be released into the atmosphere, collected, or reused in the modular bioreactor system.

In some embodiments, nutrients may be added to the aqueous culture such as, but not limited to salts, trace metals, and organic carbon. Trace metals may comprise: Iron, Copper, Molybdenum, Zinc, Cobalt, Manganese, and combinations thereof. Organic carbon sources may comprise: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, saccharose, partial or complete hydrolysates of starch, sucrose, tartaric, TCA-cycle organic acids, thin stillage, urea, industrial waste solutions, yeast extract, and combinations thereof. In some embodiments, the nutrients may be in a concentrated form. In some embodiments, the nutrients may be in a diluted form. In some embodiments, probiotic mixtures may be added to maintain the balance of microorganisms in the system. In an alternate embodiment, the system is designed to operate axenically. The term "axenic" describes a culture of an organism that is entirely free of all other "contaminating" organisms (i.e., organisms that are detrimental to the health of the microalgae or cyanobacteria culture). Throughout the specification, axenic refers to a culture that when inoculated in an agar plate with bacterial basal medium, does not form any colonies other than the microorganism of interest. Axenic describes cultures not contaminated by or associated with any other living organisms such as but not limited to bacteria, cyanobacteria, microalgae and/or fungi. Axenic is usually used in reference to pure cultures of microorganisms that are completely free of the presence of other different organisms. An axenic culture of microalgae or cyanobacteria is completely free from other different organisms. Alternately, the operation may be maintained at a low level of bacteria in the aqueous culture of microorganisms as measured less than 10,000 CFU/mL. In alternate embodiments, the bioreactor may operate with a bacteria level of $1\times10^8$ CFU/mL or less while still promoting growth of the primary microorganism of the culture.

In some embodiments, the water removal component may comprise an electrodewatering device, centrifuge, membrane, or filter. In some embodiments, the contamination control device may comprise a foam fractionation device, sonication device, antibiotic supply device, or electric field application device.

In some embodiments, the monitors and controls system may comprise a programmable logic control (PLC) system, at least one valve, and data communication hardware known in the art for monitoring and controlling pumps, lighting devices, valves, sensors, and switches for an aqueous culture bioreactor system. The monitors and controls system may receive data from the sensors and use the data to control the heat exchange, gas exchange, nutrient addition, light application, addition of culture media, and circulation flow rate in response to the sensed data to maintain the aqueous culture parameters and modular bioreactor system operation at desired levels. In some embodiments, the monitors and controls system may comprise a user interface such as, but not limited to, a graphical user interface or a touch screen interface, to allow a user to control the operation of the modular bioreactor system. In some embodiments, the at least one valve comprises an automated solenoid valve. In some embodiments, the monitors and control system may control a pump to adjust the residence time of the aqueous culture in the bioreactor module. In some embodiments, the addition of nutrients may be in concert with the application of light.

In some embodiments, the pump and control module may comprise at least one port for at least one of the operations selected from the group consisting of: the addition of culture media, the transfer of an inoculum culture of microorganisms into the modular bioreactor system, and removal of at least a portion of the aqueous culture of microorganisms for harvest. In some embodiments, the at least one port may be configured to facilitate a sterile operation to maintain axenic conditions within the modular bioreactor system and minimize the introduction of outside contamination into the modular bioreactor system. In some embodiments, the port may be configured for a quick connect/disconnect coupling to facilitate efficiency in performing an operation.

In some embodiments, the pump and control module may hold a volume of the aqueous culture on a continual basis as the aqueous culture circulates through the modular bioreactor system. When the pump and control module is decoupled from the modular bioreactor system using quick connect couplers, the culture volume is isolated in the pump and control module by the self-sealing quick connect couplers. In some embodiments, the isolated volume of the aqueous culture may be drained from the pump and control module for harvest. In some embodiments, the isolated volume of the aqueous culture may be added to another culture volume when the pump and control module is coupled to another bioreactor module. In some embodiments, all major components of the pump and control module such as, but not limited to, the de-gas tank, pump, heat exchanger, nutrient addition, gas injection, and sensors, may be isolated by double union ball valves.

One non-limiting exemplary embodiment of a pump and control module 200 is shown in FIGS. 15-20. The exemplary pump and control module 200 comprises a de-gas tank 210; a sensor manifold 250 comprising pH, temperature, dissolved oxygen, dissolved carbon dioxide, and flow rate sensors; a gas and nutrient supply manifold 240 comprising a carbon dioxide supply, an organic carbon supply, air supply, and nitrogen supply devices; a pump 260; a heat exchanger 220 utilizing chill water; a port 280 for media or inoculum addition; a port and valve 290 for harvesting; and a programmable logic control system (PLC) 230. The exemplary pump and control module 220 also comprises quick connect couplings 270 to couple to the inlet and outlet of other modules, such as cleaning and bioreactor modules, for sealed fluid communication. The pump and control module may also comprise additional components such as pumps, nutrient and gas addition manifolds, sensor manifolds, and heat exchangers disposed throughout the flow path of the pump and control module.

In one non-limiting exemplary embodiment flow path of an aqueous culture through a pump and control module, the flow path may comprise: 1) receiving a flow of the aqueous culture from a bioreactor module; 2) passing the flow through a manifold comprising parameter sensors before entering a de-gas tank; 3) passing the flow through a de-gas tank; 4) passing the flow through a manifold comprising parameter sensors after exiting the de-gas tank; 5) passing the flow through a carbon dioxide injection device to a pump; 6) pumping the flow through a flow rate sensor before entering a heat exchanger; 7) passing the flow through a heat exchanger; 8) passing the flow through a nutrient addition device after exiting the heat exchanger; 9) passing the flow through a nitrogen injection device; 10) passing the flow through an air supply device; and 11) passing the flow through a manifold comprising parameter sensors before re-entering a bioreactor module.

Multiple combinations of effective flow designs may be produced by rearranging or selectively eliminating steps of the described exemplary flow path through a pump and control module in different combinations. However, the described exemplary flow provides multiple advantages. First, by introducing carbon dioxide, or other gases (e.g., air, oxygen), into the culture medium before the pump, the gas is more effectively compressed in the aqueous culture medium before reentering the bioreactor module where the carbon dioxide or other gas may be utilized by microorganisms in a growth process during a long residency time in the turbulent flow of the bioreactor module. Second, the spaced delivery of carbon dioxide, organic carbon, nitrogen, and air with respect to the sensors facilitates a high level of mixing in the aqueous culture in the interim to get accurate readings from the sensors.

Cleaning Module

In some embodiments, the modular bioreactor system may comprise a cleaning module in direct or indirect fluid communication with at least one of a bioreactor module, and a pump and control module. In some embodiments, the cleaning module may comprise a pigging or swabbing system to circulate a Pipe Inspection Gauge (PIG) or swab through the culture tube flow path of the bioreactor module using fluid pressure, without emptying the volume of the bioreactor module or disassembly any of the modular bioreactor system components. In some embodiments, the PIG or swab may clean the interior surface of the culture tube flow path (i.e., remove organic build-up, fouling or other material) using at least one selected from the group comprising: scraping the flow path surface, brushing the flow path surface, wiping the flow path surface, and applying acoustic energy to loosen matter adhered to the flow path surface. In some embodiments, the PIG or swab may comprise a smart PIG equipped with sensors for collecting data as the smart PIG circulates through the culture tube flow path, or inspecting the surface and integrity of the tube walls. The PIG or swab may comprise any shape which fits within the culture tubes, and may conform to fit with the culture tubes or to contact the walls of the culture tubes. In some embodiments, the PIG or swab may comprise a cylindrical shape In some embodiments, the cleaning system may be operated by the programmable logic control system (PLC) in the pump and control module. In some embodiments, the PIG or swab may be used to separate the culture volume in the bioreactor module from an aqueous medium introduced into the bioreactor module as the culture volume is harvested. As the PIG or swab follows the flow path of the bioreactor module, the culture volume in front of the PIG or swab exits the bioreactor module through a harvest port and the bioreactor module volume behind the PIG or swab is filled with a new culture comprising microorganisms with no down time for the modular reactor system, as the PIG or swab both separates the culture volumes and cleans the interior surface of the culture tube flow path simultaneously.

In some embodiments, the cleaning module may comprise a system which introduces cleaning beads into the flow path of the bioreactor module. The beads may comprise small plastic or foam balls of varying density, which will distribute themselves among various levels in the aqueous medium. As the beads flow through the tube flow path, the beads may contact the interior tube surfaces and loosen material adhered to the interior tube surfaces. In some embodiments, the cleaning module may comprise a system to flush a cleaning solution (e.g., bleach solution) or steam through the bioreactor module after the volume of the aqueous culture is drained from the bioreactor module. The use of a clean solution or steam may be used to kill bacteria, degrade organic substances, or generally sterilize the interior surfaces of the bioreactor system. In some embodiments, the cleaning module may comprise quick connect couplers to couple the cleaning module to at least one of a bioreactor module, and a pump and control module in sealed fluid communication.

Figure 21:
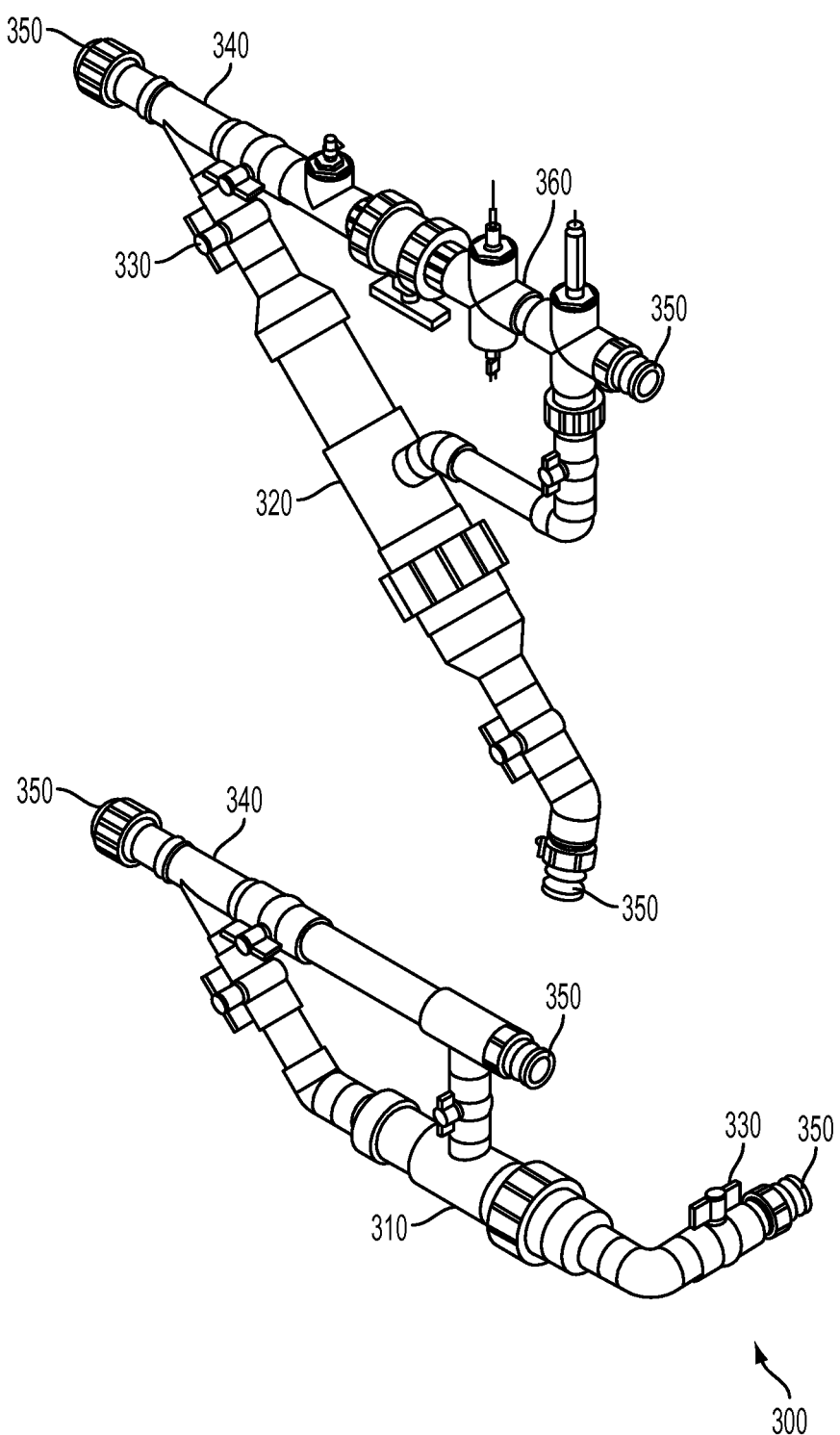
FIG. 21 shows a perspective view of an exemplary cleaning module embodiment comprising a pigging/swabbing system.

One non-limiting exemplary embodiment of a cleaning module 300 comprising a cleaning system is shown in FIG. 21. The cleaning system comprises: a swab (not shown), a snubber for launch (not shown), a snubber for catch (not shown), a launch chamber 310, a catch chamber 320, a plurality of valves 330 to control the flow and pressure in the modular bioreactor system, and 45 degree tees 340. The cleaning system also comprises quick connection couplers 350 to couple the cleaning system to a bioreactor module and a pump and control module. The cleaning system may also comprise a sensor manifold 360, with at least one of pH, temperature, dissolved oxygen, and dissolved oxygen sensors.

Strategic Lighting Embodiment

In some embodiments, the bioreactor may be equipped with a more efficient configuration for applying light to a culture of microorganisms using strategically placed lighting devices. The at least one lighting device may be strategically placed in the bioreactor module to create a lit section or incrementally lit sections of the bioreactor module. With strategically placed lighting devices, the culture of microorganisms flowing through the bioreactor module may be exposed to light only when passing by a strategically placed lighting device, thus creating a prescribed duty cycle and frequency of light exposure, effectively using lights in conjunction with the flow velocity to create duty cycle or a flashing/pulsing affect with lighting devices that are emitting light continuously. The duty cycle may be generated by choosing flow paths and lighting device sizes such that only a specific fraction of the bioreactor module volume is lit. Frequency may be controlled by modulating the flow velocity of the aqueous culture medium, such as with a pump and control system, in such a way as to move the microorganism in and out of the bioreactor module lit sections at the desired frequency, with the frequency increasing as the flow rate increases. In some embodiments, a bioreactor module with strategic lighting may comprise fewer lighting devices and use less energy than a bioreactor module simultaneously applying light to the entire aqueous culture volume or utilizing flashing lights to generate a duty cycle. In some embodiments, by applying a lighting device directly to the exterior of a transparent tubular flow path at least 90%, 95%, or 99% of the light emitted by the lighting device may be transmitted into the inner volume of the transparent tubular flow path.

Figure 22:
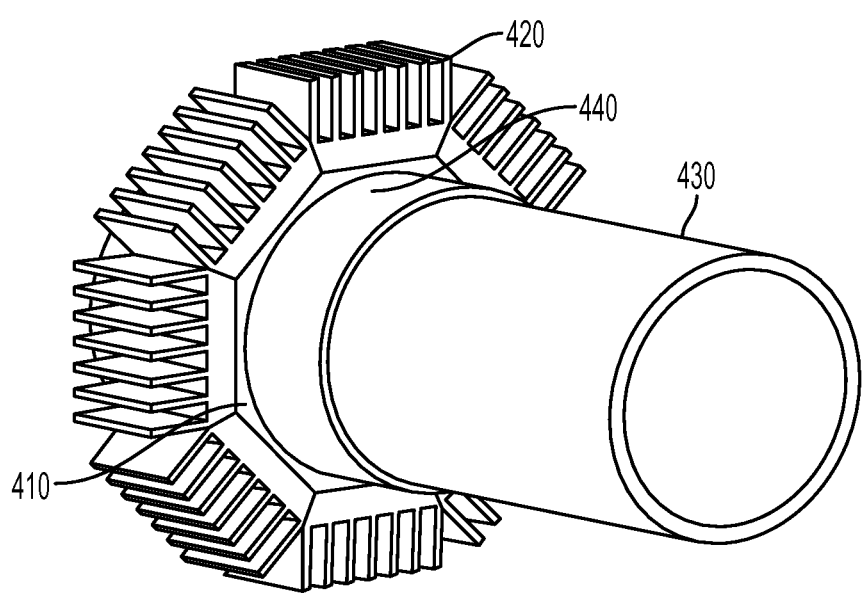
FIG. 22 shows a perspective view of an exemplary strategic lighting device embodiment disposed on a culture tube segment.
Figure 23:
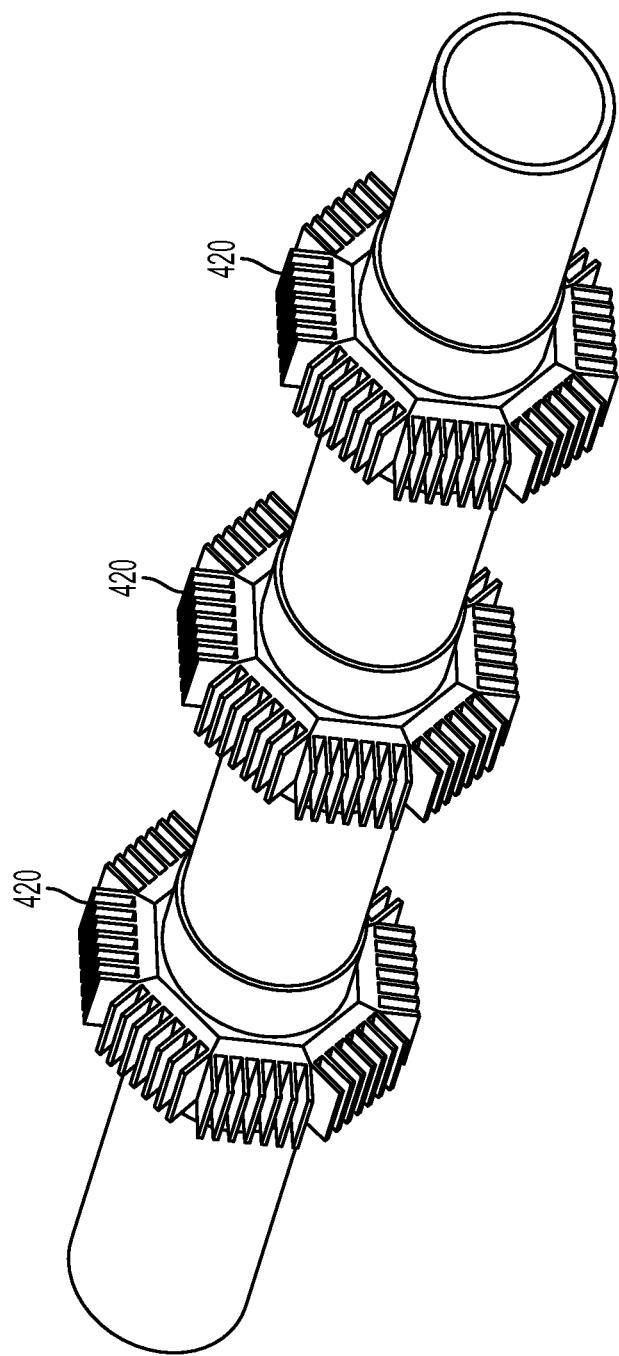
FIG. 23 shows a perspective view of multiple strategic lighting devices disposed on a culture tube segment.

One non-limiting exemplary embodiment of a bioreactor module comprising a tubular flow path with strategic lighting is shown in FIGS. 22-23. As shown in FIG. 22, at least one lighting device 420 may be disposed directly on a transparent segment of a tube 410. The at least one lighting device 420 may comprise a ring or clamp encircling the tube segment with LEDs transmitting light directly into the interior of the tube segment 410 with no blockage of light from overlapping tube segments or other components of the bioreactor module. In some embodiments, the entire tube may be transparent. In some embodiments, transparent tube section 410 may be coupled to a non-transparent tube section 430 by a connector 440 or the transparent tube may comprise a section covered or coated with an opaque material, and thus the tube section may only be transparent at the location of the at least one lighting device. As shown in FIG. 23, a plurality of lighting devices 420 may be spaced on a tubular flow path to generate a lighting duty cycle. In some embodiments the lighting devices may be spaced equally along the length of the tube segment. In some embodiments, the lighting devices may have unequal spacing along the length of the tube segment. In another embodiment, the strategic lighting device comprises at least one flexible sheet of micro-LEDs wrapped around a tube segment. In another embodiment, the strategic lighting device, such as a plurality of LEDs, may be embedded directly in the wall of a tube segment.

Mixotrophic Bioreactor Embodiment

In some embodiments, the modular bioreactor system may be configured specifically for culturing microorganisms in mixotrophic conditions. The mixotrophic bioreactor module may comprise at least one lighting device and a closed bioreactor configuration, such as a tubular bioreactor. The mixotrophic pump and control module may comprise pH, dissolved oxygen, and dissolved carbon dioxide sensors; a gas supply device (e.g., carbon dioxide, oxygen, air); and an organic carbon supply device. In some embodiments, the mixotrophic pump and control module may not comprise a de-gas tank or air injection system. Instead of utilizing air injection and a de-gas tank for gas exchange, the mixotrophic pump and control module may use a programmable logic control system (PLC) to monitor the pH, dissolved oxygen, and dissolved carbon dioxide levels in the aqueous culture to facilitate the exchange of gases in the closed flow path of bioreactor module.

The PLC may control the administration of organic carbon and gases (e.g., carbon dioxide, oxygen, air) to the aqueous culture of microorganisms in order to maintain the pH at an optimal level based on the sensor input from the dissolved oxygen and dissolved carbon dioxide sensors. The PLC may control the administration of carbon dioxide when the dissolved oxygen level is a below a threshold level, in order to facilitate the use of light and carbon dioxide by the microorganisms for growth and oxygen production. The amount of carbon dioxide administered may also be determined by the detected dissolved carbon dioxide level. The PLC may control the administration of organic carbon when the dissolved oxygen level is above a threshold level, in order to facilitate the use of organic carbon by the microorganisms for growth and carbon dioxide production. The elimination of air injection and a de-gas tank from the pump and control reduces the amount of unutilized gases diffusing out of the culture medium and the amount of foam in the bioreactor; as well as reducing the amount of equipment, size of the module, and weight of the module in comparison to both strictly phototrophic and strictly heterotrophic configured systems. Additionally, the efficient gas supply and consumption in a mixotrophic modular bioreactor system is closer to carbon neutral than both strictly phototrophic and strictly heterotrophic configured systems. In other embodiments, the mixotrophic pump and control module may comprise a de-gas tank, and/or an air injection device.

In some embodiments, an organic carbon source may be added in limited supply to the aqueous culture when the dissolved oxygen rises above 125% or 150% or greater than 200% saturation. The organic carbon may be consumed by the microorganisms in the aqueous culture in a fractional length of a bioreactor flow path.

Sensor Manifold Embodiment

In some embodiments, the sensor manifold may be optimized to reduce flow stagnation zones which facilitate biofouling on the interior surface of the manifold and may affect the sensor data. A sensor manifold may comprise at least one sensor disposed in a seamless manifold and sanitary fittings or clamps on each side, which may reduce the overall envelope and flow stagnation zones compared to a traditional manifold comprising seams from glued PVC joints. In some embodiments, the manifold is constructed from stainless steel. Hollow bungs for mounting the at least one sensor may be welded directly to the stainless steel manifold with a saddle shape in line with the curved profile of the manifold, to reduce the stagnation zones created by the recessed or protruding flat surfaces of standard PVC tees with reducing bushings that do not follow the curved profile of the flow path surfaces. The tight fit for the sensors in the custom bungs may also be enhanced with an o-ring at the base of the bung to prevent fluid from flowing upwardly through the bung when a sensor is mounted within the bung. The custom welded bungs also provide more precise positioning for the sensors in the fluid flow path of the interior volume of the bung to minimize disruption of the flow boundaries. A seamless, stainless steel manifold also provides the option of using high pressure steam or autoclaving for cleaning and sterilizing the manifold.

Figure 24:
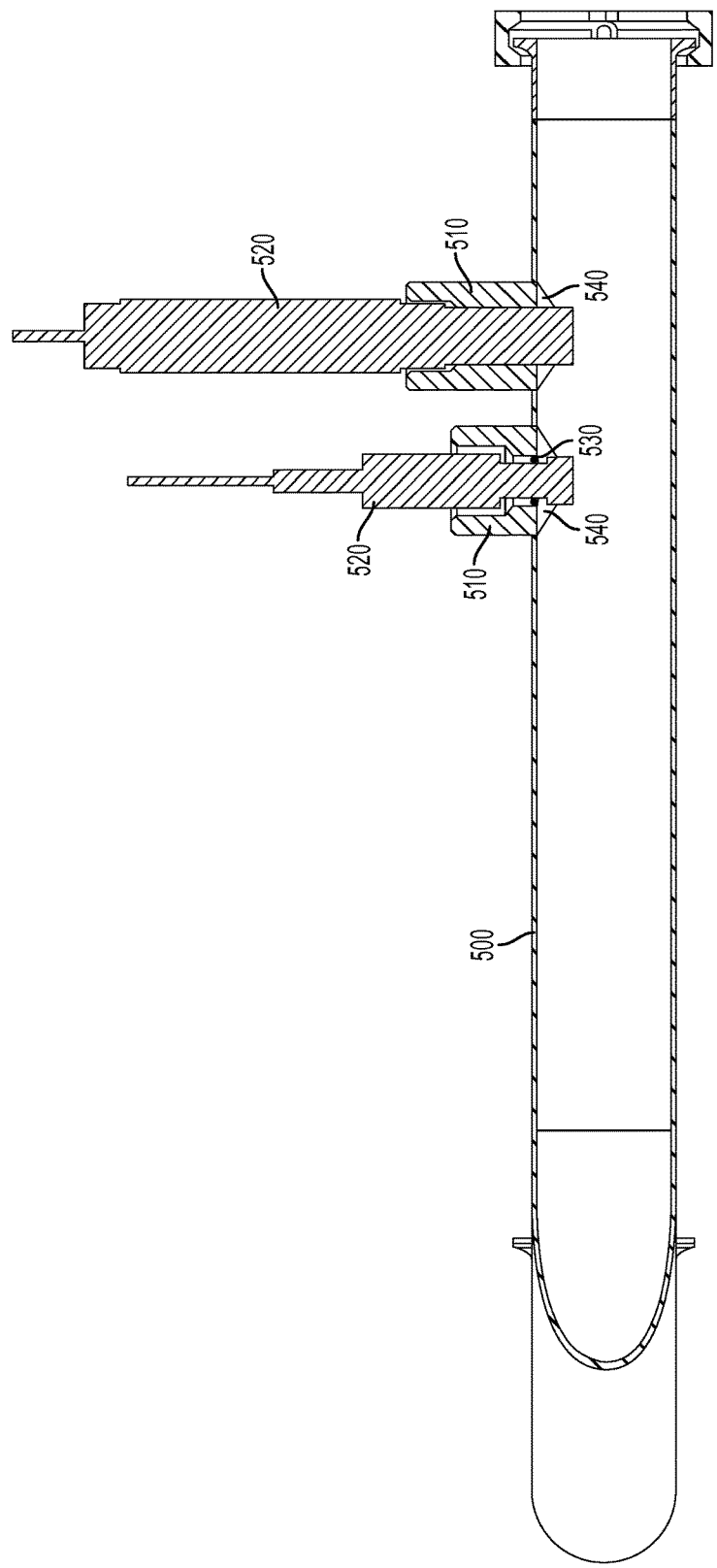
FIG. 24 shows a longitudinal cross-sectional view of an exemplary sensor manifold embodiment.
Figure 25:
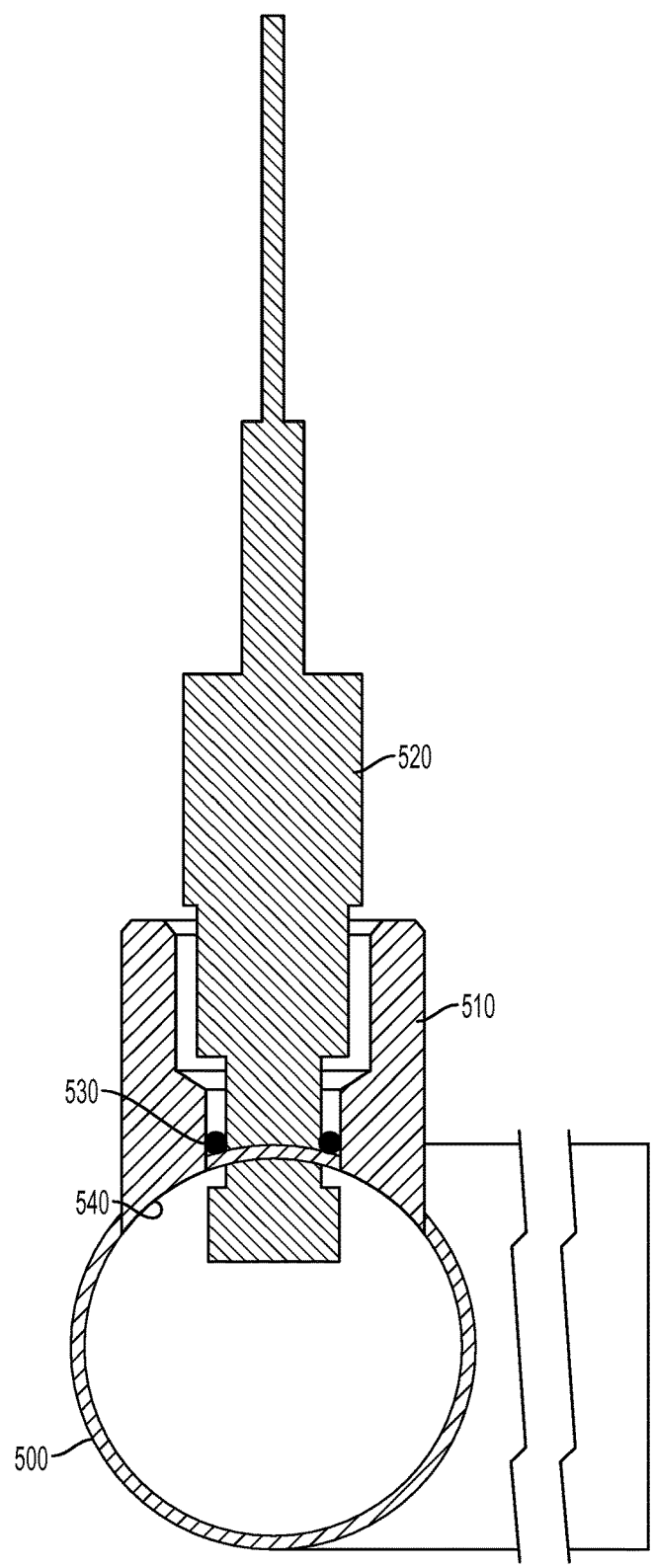
FIG. 25 shows a cross-sectional view of an exemplary sensor manifold embodiment.

One non-limiting exemplary embodiment an optimized sensor manifold is shown in FIGS. 24-25. The cross-section views in FIG. 24-25 shows a seamless manifold 500 and custom welded bungs 510 holding the sensors 520 with the sensor probe head precisely disposed in the flow path of the manifold. The saddle shaped base surface 540 of the bung 510 follows the curved profile of the manifold 500 to minimize disruptions in the flow boundaries. An o-ring 530 disposed between the bung 510 and sensor 520 allows the sensor head to be strategically placed in the flow path of the manifold 500 and prevents liquid culture medium from flowing upwardly through the bung.

Cascading Transfer Bioreactor System

The above described modular bioreactor system may be used in a cascading transfer bioreactor system. The cascading transfer bioreactor system, as shown in the diagram in FIG. 28, may comprise a plurality of bioreactor modules of different volumes, which start an aqueous culture of microorganisms in the bioreactor module with the smallest volume. Once the culture reaches a certain stage in microorganism density and maturity, the entire volume may be transferred to the bioreactor module of the next biggest volume. The culture growth and transfer process to a larger volume may be repeated multiple times until the volume is sufficient to inoculate a final or production bioreactor.

Figure 28:
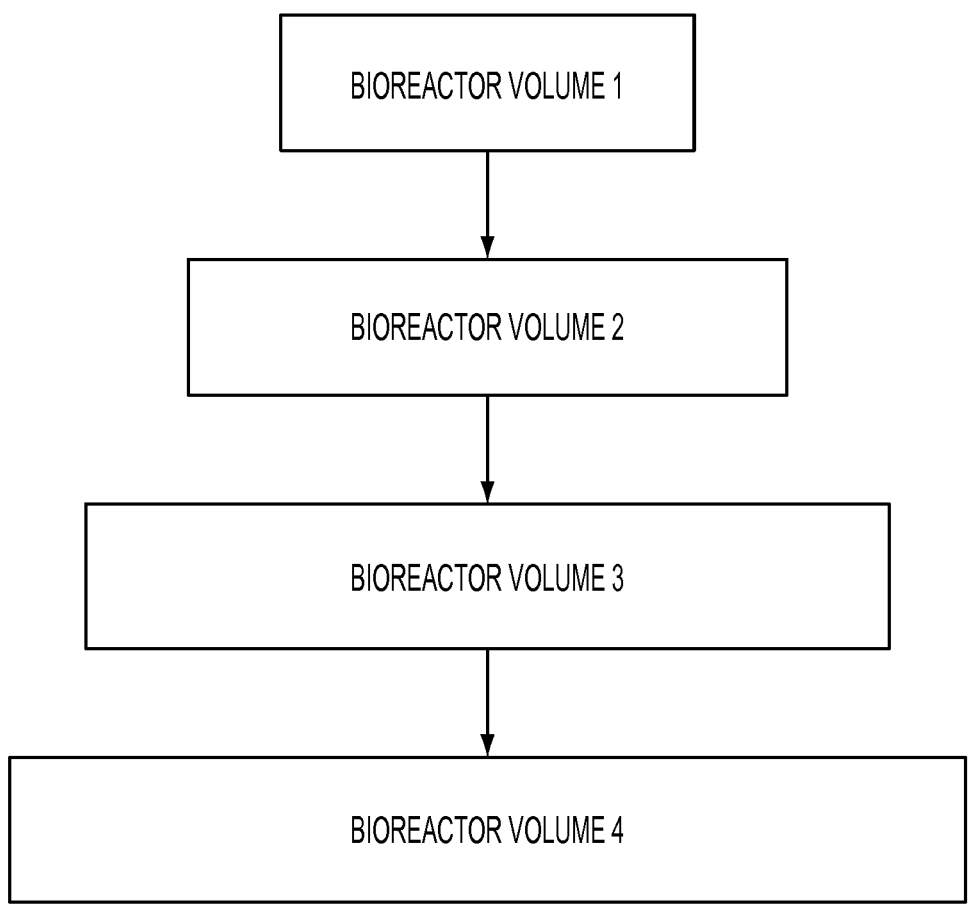
FIG. 28 shows a diagram of an exemplary cascading transfer bioreactor system embodiment.

As shown in diagram of FIG. 28, Bioreactor Volume 1 has the smallest volume of the bioreactor modules and starts with an inoculum of a microorganism culture. Once the culture in Bioreactor Volume 1 reaches a critical density and maturity, the entire volume is transferred to the larger Bioreactor Volume 2 in a separate bioreactor module. Once the culture in Bioreactor Volume 2 reaches a critical density and maturity, the entire volume is transferred to the larger Bioreactor Volume 3 in a separate bioreactor module. Once the culture in Bioreactor Volume 3 reaches a critical density and maturity, the entire volume is transferred to the larger Bioreactor Volume 4 in a production bioreactor module. While the example shown in FIG. 27 demonstrates four stages of increasing bioreactor volume, the cascading transfer concept may be implemented in any number of bioreactor modules with increasing volume comprising at least two bioreactors of different volumes. In some embodiments, each bioreactor module may be coupled to other bioreactor modules for fluid communication through a manifold. In some embodiments, each transfer between bioreactors occurs as a transfer sealed from the outside environment and outside contamination.

Figure 29:
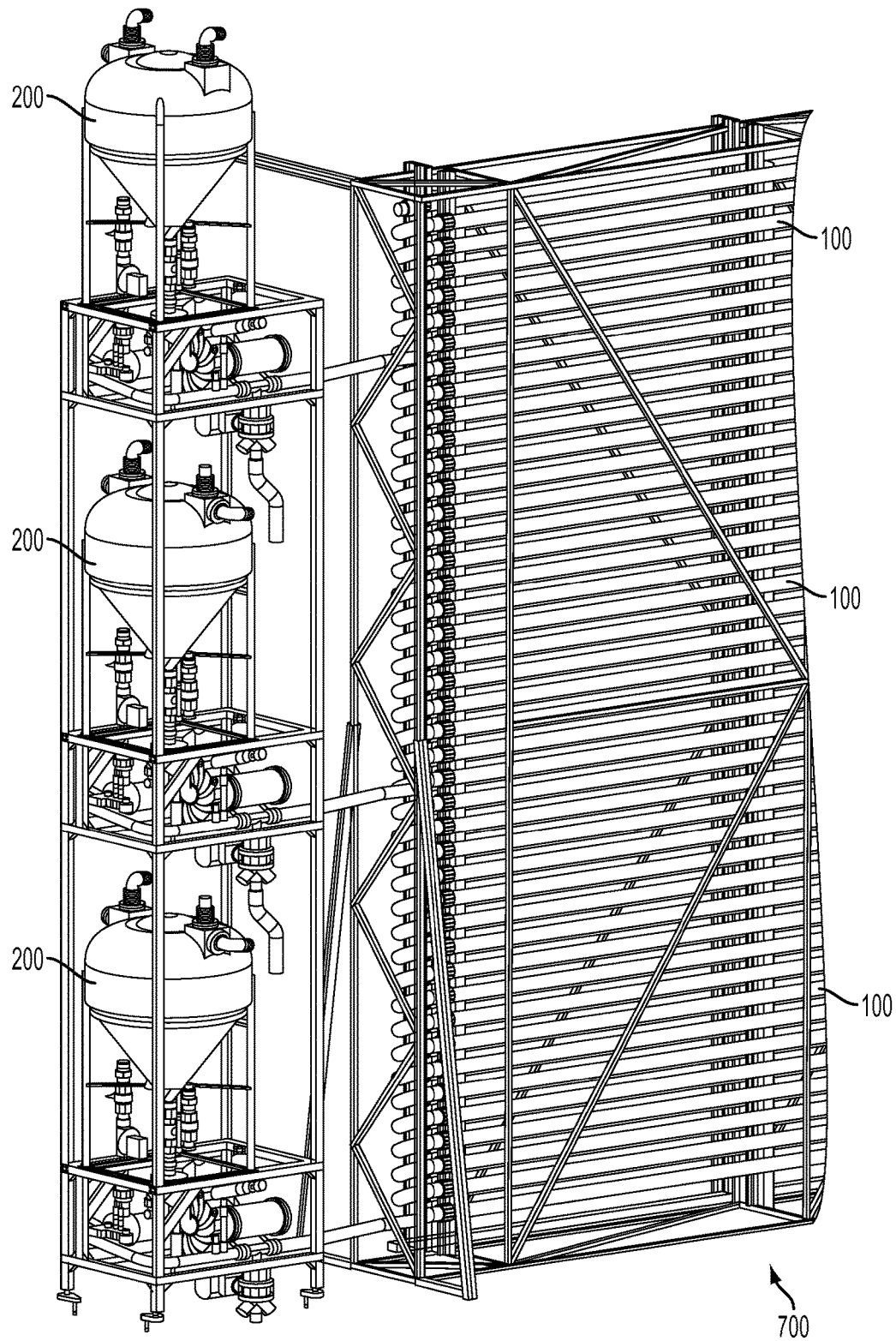
FIG. 29 shows a perspective partial view of an exemplary cascading transfer bioreactor system embodiment.

Each bioreactor module may be isolated from fluid communication with the other bioreactor modules. In some embodiments, the cascading transfer bioreactor system may comprise a plurality of pump and control modules. In some embodiments, the cascading transfer bioreactor system may comprise a plurality of cleaning modules. In some embodiments, the cascading transfer bioreactor system may comprise an automated system to facilitate the harvest and transfer between bioreactor modules without exposing the culture volume to the environment or outside contamination. One non-limiting exemplary embodiment of the cascading transfer bioreactor system 700 with multiple bioreactor modules 100 and multiple pump and control modules 200 is shown in the partial view of FIG. 29.

The cascading transfer bioreactor system comprising modular bioreactors may be used as a production platform, as a seed reactor platform, or a combination of both. The cascading transfer bioreactor system may be used in a system that connects the seed production with one or more larger volume downstream production reactors. The cascading transfer bioreactor system may be partially or fully harvested to inoculate a larger seed reactor. The cascading transfer bioreactor system may be used as a finishing step for the production of products that require a two-step growth process to produce pigments or other high value products.

In an alternate embodiment, the cascading transfer bioreactor system may comprise culture tube segments that have different diameters, where a small diameter is used for a preferentially phototrophic section while a larger tubular diameter is used for a preferably mixotrophic section. The segments with different culture tube diameters may be interleaved and connected in a way to enhance turbulence or mixing in the system without the use of a high Reynolds numbers such that the overall system pressure drop is reduced.

Those skilled in the art will recognize, or be able to ascertain, using no more than routine experimentation, numerous equivalents to the specific embodiments described specifically herein. Such equivalents are intended to be encompassed in the scope of the following claims.

| Call Out List | |
|---|---|
| Element No. | Description |
| 10 | Modular bioreactor system |
| 100 | Bioreactor module |
| 110 | Structural frame segments |
| 120 | Carrier |
| 130 | Swiveling panels |
| 140 | Straight culture tube segments |
| 141 | U-bend culture tube segments |
| 142 | Tube segment connector |
| 143 | First vertical array of tube segments |
| 144 | Second vertical array of tube segments |
| 145 | Bioreactor quick connect couplers |
| 150 | Lighting devices |
| 200 | Pump and control module |
| 210 | De-gas tank |
| 220 | Heat exchanger |
| 230 | Programmable logic control system (PLC) |
| 240 | Gas and nutrient supply manifold |
| 250 | Sensor manifold comprising sensors |
| 260 | Pump |
| 270 | Pump and control quick connect couplers |
| 280 | Port for media or inoculum addition |
| 290 | Harvest port and valve |
| 300 | Cleaning module |
| 310 | Launch chamber |
| 320 | Catch chamber |
| 330 | Valves |
| 340 | 45 degree Tees |
| 350 | Cleaning quick connect couplers |
| 360 | Sensor manifold |

-continued

| Call Out List | |
|---|---|
| Element No. | Description |
| 410 | Transparent tube segment |
| 420 | Lighting device |
| 430 | Non-transparent tube segment |
| 440 | Connector |
| 500 | Sensor manifold |
| 510 | Bung |
| 520 | Sensor |
| 530 | O-ring |
| 540 | Saddle shaped base surface |
| 600 | Flexible strap |
| 610 | Grommet |
| 620 | Turnbuckle |
| 700 | Cascading transfer bioreactor system |
| 800 | Sun |
| 810 | Sunlight |

What is claimed is:

1. A bioreactor, comprising:
  a. A plurality of culture tube segments comprising:
    i. a longitudinal axis along the length of the tube segments;
    ii. an interior volume;
    iii. a circular cross section of a diameter D; and
  b. A support frame comprising at least one vertically oriented culture tube carrier configured to support the plurality of culture tube segments on opposing horizontal first and second sides of the carrier in a horizontally staggered and vertically spaced arrangement, wherein
    (a) at least a portion of the circular cross section of a plurality of culture tube segments on the first side overlaps on a horizontal plane intersecting the circular cross-section of at least an equal number of the plurality of culture tube segments, and
    (b) the horizontal plane travels a total distance less than or equal to D/2, and
    (c) a plurality of the culture tube segments on the first side vertically overlap each other across the entire longitudinal axis and a plurality of the culture tube segments on the second side vertically overlap each other across the entire longitudinal axis;
  c. A pump comprising an intake and an outlet; and
  d. A gas supply device, wherein the gas supply device is disposed before the pump intake in a flow path of an aqueous culture of the bioreactor.

2. The bioreactor of claim 1, wherein the plurality of culture tube segments are coupled together in series to form a single helical tubular flow path, the plurality of culture tube segments further comprising;
  a. At least one U-bend culture tube segment;
  b. A plurality of straight culture tube segments; and
  c. At least one connector configured to couple together the ends of the at least one U-bend culture tube segment and the plurality of straight culture tube segments together in fluid communication in series to form a single helical tubular flow path.

3. The bioreactor of claim 2, further comprising at least one lighting device configured to emit light towards the plurality of culture tube segments.

4. The bioreactor of claim 3, wherein 100% of the light emitted from the at least one lighting device traveling on a horizontal plane intersecting the circular cross-section of at least one of the plurality of straight culture tube segments in a direction normal to the longitudinal axis of the culture tube segments strikes an exterior surface of the straight culture tube segments.

5. The bioreactor of claim 1, wherein the culture tube segments comprise separate flow paths that are not connected.

6. The bioreactor of claim 1, further comprising at least one sensor selected from the group consisting of: pH sensor, dissolved oxygen sensor, dissolved carbon dioxide sensor, and temperature sensor.

7. The bioreactor of claim 1, further comprising an organic carbon supply device.

8. The bioreactor of claim 1, wherein the culture tube segments further comprise baffles disposed on an interior surface of the culture tube segments.

9. The bioreactor of claim 1, wherein except for the horizontal plane there is direct light path from the area above or below the exterior of the culture tube segment of the first side to the corresponding area above or below the exterior of the second side.

10. The bioreactor of claim 1, wherein there is both a top area of overlap and bottom area of overlap in the horizontal plane between a plurality of culture tube segments on the first side and a plurality of culture tube segments on the second side wherein each of the two areas of overlap travel a distance of less than or equal to D/2.

* * * * *